(12) United States Patent
Prausnitz et al.

(10) Patent No.: US 8,690,865 B2
(45) Date of Patent: Apr. 8, 2014

(54) METHODS AND DEVICES FOR THERMAL TREATMENT

(75) Inventors: Mark R. Prausnitz, Atlanta, GA (US); Mark G. Allen, Atlanta, GA (US); Jung-Hwan Park, Smyrna, GA (US); Yong-Kyu Yoon, Smyrna, GA (US); Jin-Woo Park, Suwanee, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1467 days.

(21) Appl. No.: 11/597,969

(22) PCT Filed: May 31, 2005

(86) PCT No.: PCT/US2005/019035
§ 371 (c)(1),
(2), (4) Date: Aug. 15, 2007

(87) PCT Pub. No.: WO2006/004595
PCT Pub. Date: Jan. 12, 2006

(65) Prior Publication Data
US 2008/0045879 A1 Feb. 21, 2008

Related U.S. Application Data

(60) Provisional application No. 60/575,717, filed on May 28, 2004.

(51) Int. Cl.
*A61B 18/08* (2006.01)
*A61N 1/30* (2006.01)

(52) U.S. Cl.
USPC .................................. 606/28; 604/19; 604/20

(58) Field of Classification Search
USPC ........................ 606/27–50, 131, 159; 607/96; 604/19–20, 200, 500, 290; 600/309–310, 316, 365, 573
See application file for complete search history.

(56) References Cited

U.S. PATENT DOCUMENTS 5,983,131 A * 11/1999 Weaver et al. .................. 604/20
6,181,963 B1   1/2001 Chin et al.
6,251,100 B1   6/2001 Flock et al.
(Continued)

FOREIGN PATENT DOCUMENTS

WO         0074763         12/2000

OTHER PUBLICATIONS

Badkar, Advait V. et al., "Transdermal Delivery of Interferon Alpha-2B Using Microporation and Iontophoresis in Hairless Rats", Pharmaceutical Research, vol. 24, No. 7, pp. 1389-1395, Jul. 7, 2007.

(Continued)

*Primary Examiner* — Ronald Hupczey, Jr.
(74) *Attorney, Agent, or Firm* — Troutman Sanders LLP; Ryan A. Schneider

(57) ABSTRACT

The present invention comprises methods and devices for thermal treatment of a barrier to increase the permeability of the barrier. One form of increasing the permeability of the barrier comprises forming micropores which may be used for administration of active agents across the barrier, or may be used for sampling or collecting fluids, or may be used for detecting, measuring or determining analytes, or may be used for monitoring of physiological or other conditions. Devices of the present invention may comprise microheaters that are activated by inductive or ohmic heating power supply components.

12 Claims, 11 Drawing Sheets

(56) References Cited

U.S. PATENT DOCUMENTS

| | | | |
|---|---|---|---|
| 6,527,716 B1* | 3/2003 | Eppstein | 600/309 |
| 6,603,998 B1* | 8/2003 | King et al. | 604/20 |
| 6,689,380 B1 | 2/2004 | Marchitto et al. | |
| 6,730,028 B2* | 5/2004 | Eppstein et al. | 600/309 |
| 7,113,821 B1* | 9/2006 | Sun et al. | 604/21 |
| 7,133,717 B2* | 11/2006 | Coston et al. | 604/20 |
| 7,164,942 B2* | 1/2007 | Avrahami et al. | 604/20 |
| 7,578,954 B2* | 8/2009 | Gartstein et al. | 264/154 |
| 7,758,561 B2* | 7/2010 | Eppstein | 604/500 |
| 2001/0023330 A1* | 9/2001 | Palti | 604/20 |
| 2003/0225362 A1 | 12/2003 | Currie et al. | |
| 2004/0039343 A1* | 2/2004 | Eppstein et al. | 604/200 |
| 2006/0264805 A1* | 11/2006 | Singh et al. | 604/20 |

OTHER PUBLICATIONS

Banga, Ajay K., "New Technologies to Allow Transdermal Delivery of Therapeutic Proteins and Small Water-Soluble Drugs", American Journal of Drug Delivery, vol. 4, No. 4, pp. 221-230, 2006.

Birchall, James et al., "Cutaneous Gene Expression of Plasmid DNA in Excised Human Skin Following Delivery Via Microchannels Created by Radio Frequency Ablation", International Journal of Pharmaceutics, vol. 312, pp. 15-23, 2006.

Bramson, J. et al., "Enabling Topical Immunization via Microporation: A Novel Method for Pain-Free and Needle-Free Delivery of Adenovirus-Based Vaccines", Gene Therapy, vol. 10, pp. 251-260, 2003.

Levin, Galit et al., "Transdermal Delivery of Human Growth Hormone Through RF-Microchannels", Pharmaceutical Research, vol. 22, No. 4, pp. 550-555, Apr. 2005.

Sintov, Amnon C. et al., "Radiofrequency-Driven Skin Microchanneling as a New Way for Electrically Assisted Transdermal Delivery of Hydrophilic Drugs", Journal of Controlled Release, vol. 89, pp. 311-320, 2003.

Supplementary Partial European Search Report dated Mar. 12, 2010 for related European Application No. 05785712.

Int'l Search Report and Written Opinion for PCT/US2005/019035 dated Mar. 21, 2006.

* cited by examiner

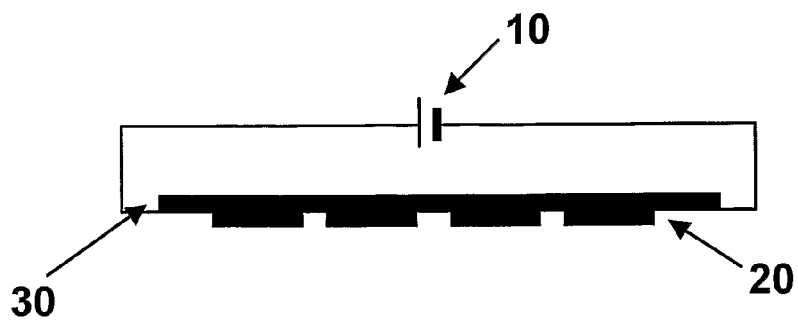
Fig. 1a
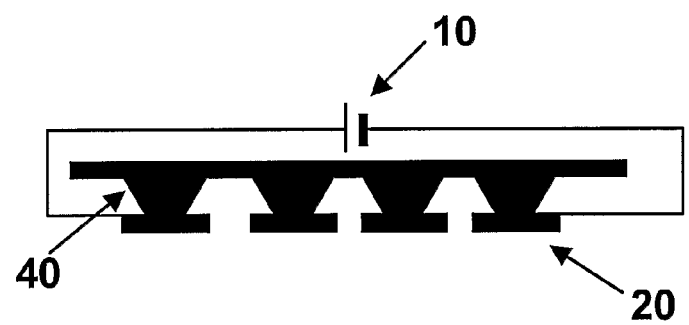
Fig. 1b
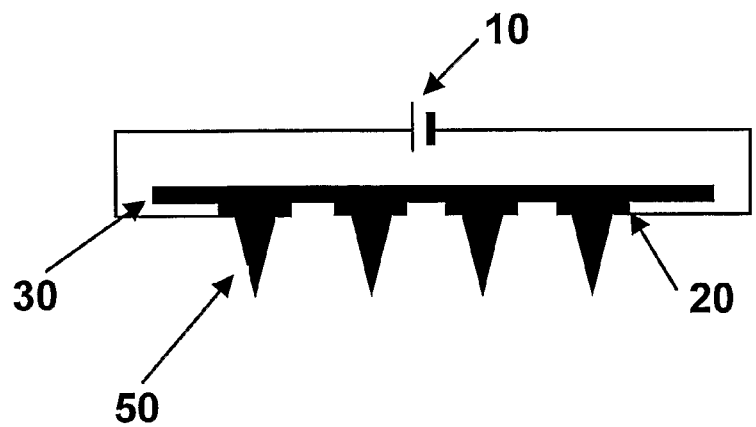
Fig. 1c
Fig. 1

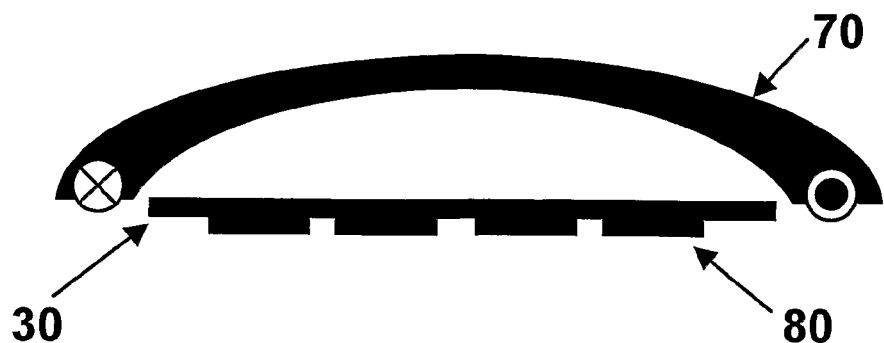
Fig. 2a
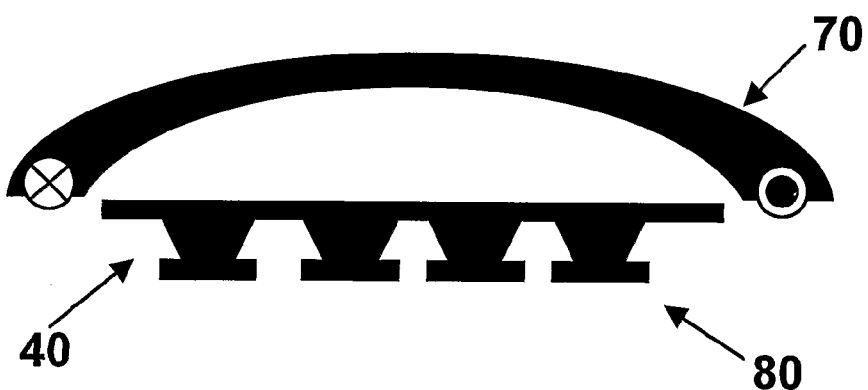
Fig. 2b
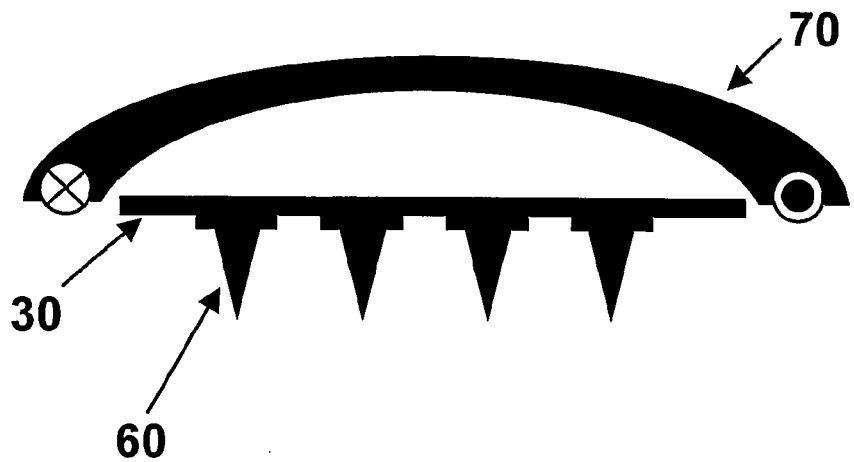
Fig. 2c
Fig. 2

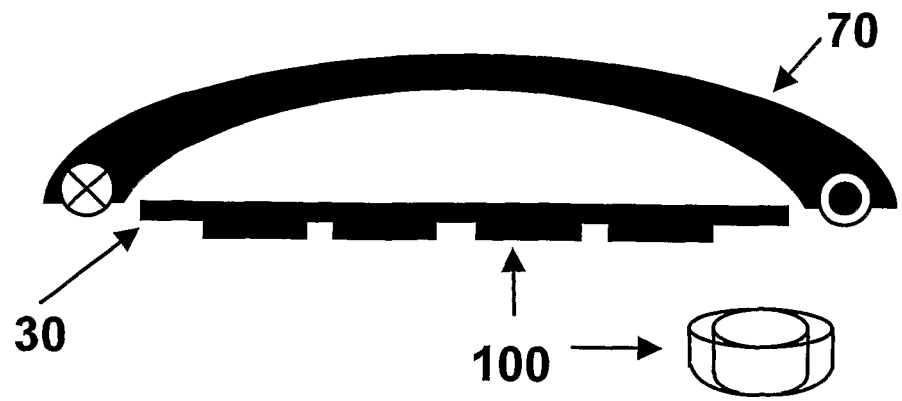
Fig. 2d
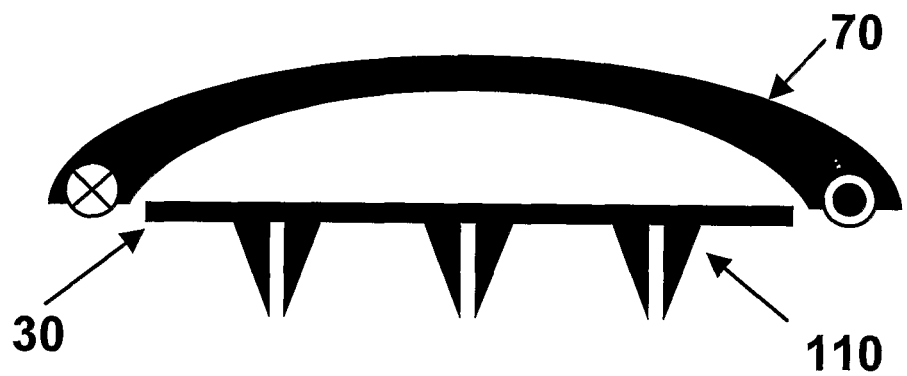
Fig. 2e
Fig. 2

METHODS AND DEVICES FOR THERMAL TREATMENT

RELATED APPLICATIONS

This application claims the priority of U.S. Provisional Patent Application No. 60/575,717, filed May 28, 2004, which is herein incorporated in its entirety.

BENEFIT CLAIMS

This application is a US National Stage of International Application No. PCT/US2005/019035, filed 31 May 2005, which claims the benefit of U.S. Provisional Application No. 60/575,717, filed 28 May 2004.

GOVERNMENT LICENSE RIGHTS

The U.S. Government has a paid-up license in this invention and the right in limited circumstances to require the patent owner to license others on reasonable terms as provided for by the terms of Contract No. 8-ROI-EB00260-03 awarded by the National Institutes of Health, and under Contract No. F33615-02-C-1160, awarded by the U.S. Air Force.

TECHNICAL FIELD

The present invention relates to methods using MEMS thermal treatment devices for increasing the permeability of barriers, for example by creating openings in barriers, such as skin, for providing active agents across the barriers, or for providing sites from which analytes can be retrieved and measured.

BACKGROUND OF THE INVENTION

Transdermal delivery of certain drugs has been possible for many years. Transdermal drug delivery devices are generally laminated composites that include a pressure-sensitive adhesive layer which may contains the drug and by which the device is attached to the skin and a backing layer which forms the outer surface of the device, which may form a reservoir for the drug, and which is impermeable to the drug. To date, commercial exploitation of transdermal drug delivery systems has been limited to only a few specific active agents, because of the practical problems to be overcome. These problems include the solubility of the drug, the effect of the drug on the adhesive layer and delivery of the drug to the skin and through the stratum corneum and viable epidermis into the systemic circulation at a constant rate over a prolonged period. In addition, transdermal drug delivery devices must maintain their integrity during storage prior to use.

Transdermal delivery is difficult because of skin's highly impermeable outer layer called stratum corneum. The stratum corneum is 10-20 µm thick and, unlike other tissues in the body, contains "cells" filled with bundles of cross-linked keratin and keratohyalin surrounded by an extracellular matrix of lipids assembled in multiple bilayer structures. There are no blood vessels or nerves in stratum corneum. Below stratum corneum is the viable epidermis, which is 50-100 µm thick and also contains no blood vessels, but has some nerves. Deeper still is the dermis, which measures 1-2 mm thick and contains blood vessels, lymphatics and nerves. Drugs that cross the stratum corneum barrier can generally diffuse to the capillaries in the superficial dermis for absorption and systemic distribution. For this reason, most approaches to increase transdermal delivery have emphasized disruption of stratum corneum microstructure using chemical or physical methods.

Conventional drug delivery using pills or injection is often not suitable for most protein or biotech active agents, DNA and other nucleic acid constructs, and other therapies currently proposed and envisioned. An attractive alternative would be transdermal delivery from a patch, which avoids degradation in the gastrointestinal tract and first-pass effects of the liver associated with oral delivery as well as the pain and inconvenience of intravenous injection. Transdermal drug delivery also offers the possibility to continuously control the delivery rate, in contrast to conventional methods that deliver a large, discrete bolus. These advantages have led to a multi-billion dollar market for transdermal patches used for smoking cessation (nicotine), hormone replacement (estradiol), and other indications. Despite these advantages, transdermal drug delivery is severely limited by the poor permeability of human skin; most drugs do not cross skin at therapeutic rates and only a dozen drugs have been approved by FDA for transdermal delivery since the first patch was introduced 25 years ago. The skin's barrier properties are due to the highly impermeable outer layer called stratum corneum, which is 10-20 µm thick. Drugs that cross the stratum corneum barrier can generally diffuse to deeper capillaries for systemic distribution. For this reason, most approaches to increase transdermal delivery have emphasized disruption of stratum corneum microstructure using chemical or physical methods. Currently approaches exist to physically disrupt the stratum corneum using heating filaments or an array of electrodes to generate Joule heating by passing a short, high-current electric pulse. These devices are all powered by means of wires physically connected to an external DC or RF power supply.

What is needed are methods and devices that can increase the permeability of barriers, such as skin, that do not require the physical connection of wires to link the power supply to the components that are causing the increase in permeability. Further, what is needed are methods and devices that provide for transdermal transfer of a greater variety of active agents. Additionally, what is also needed are methods and devices that can aid in detecting and measuring analytes that are contained within a barrier, particularly skin or other membranes.

SUMMARY OF THE INVENTION

The present invention comprises methods and devices using heat to increase the permeability of barriers, for example to create micropores in barriers, such as the inner and outer membranes of humans, animals, plants and other living organisms, or barriers used in industrial applications. For example, methods of the present invention comprise minimizing the barrier properties of an inner or outer membrane, such as stratum corneum, using thermal treatment of the membrane to provide micropores through which active agents may be provided through the stratum corneum to the organism or from which one may controllably collect fluids or analytes from within the body to enable the monitoring or detection of these analytes. Methods comprise porating one or more selected areas of a barrier, thereby reducing the barrier properties of the barrier, using thermal treatment by microheaters. The microheaters are heated by ohmic or inductive heating. The microheaters may provide controlled, precise thermal ablation and create a micropore in the barrier. The microheaters may be used to create micropores in the barrier and may then be removed or remain in place.

The micropores formed in the barrier provide for methods for delivery of active agents through the barrier, such as transdermal delivery of drugs, nucleic acids, gene therapy molecules, or molecules that are not amenable to standard transdermal delivery. The micropores formed in the barrier can be used as sites for sampling fluids, monitoring, measuring or detecting analytes from the interior of the barrier, such as for monitoring glucose in a human or animal.

An aspect of the invention comprises thermal treatment devices decreasing the barrier properties of a barrier, for example by providing micropores in a barrier comprising a power supply component and a microheater component. The thermal treatment device may comprise both components in a single unitary device, wherein the components are in physical connection such as by a wire, or the components may be in separate units that may not be connected by physical attachment, such as a wire. Wireless devices, comprising a power supply component not physically attached to the microheater component, may provide energy to the microheater component and activate the microheaters by inductive heating.

An aspect of the invention comprises a microheater component comprising one or more microheaters associated with a transdermal delivery patch comprising at least one active agent and a separate inductive energy supply component. In use of such a device, methods comprise applying the microheater component comprising the transdermal delivery patch to the skin of a living organism, bringing the energy supply component close enough to the microheaters so as to heat the microheaters using inductive heating, forming micropores in the skin adjacent to the microheaters, removing the energy supply component, and allowing the microheater component comprising the transdermal delivery patch to remain associated with the skin and provide the active agent to the living organism. The microheaters of the present invention may or may not comprise rapid volume change materials. Such ablation materials may be applied to a barrier prior to or simultaneously with contact by the microheaters.

BRIEF DESCRIPTION OF DRAWINGS

FIG. 1a-c are profile diagrams of microheaters, activated by ohmic power supply.

FIG. 2a-e are profile diagrams of microheaters, activated by inductive heating power supply.

DETAILED DESCRIPTION

Figure 3:
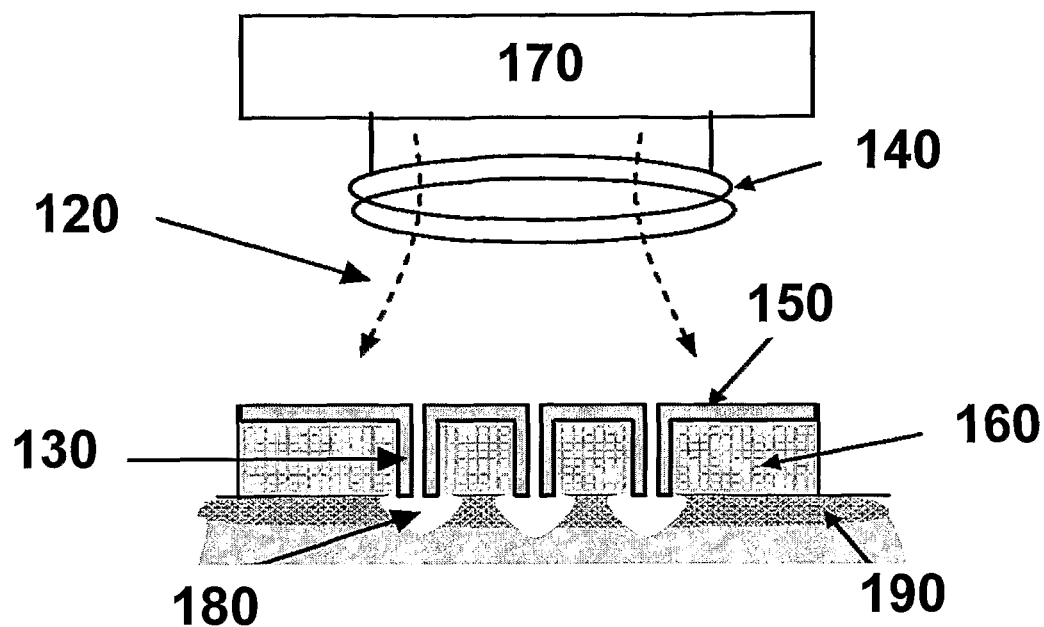
FIG. 3 is a diagram of activation of hollow post microheaters by an inductive heating power supply component.

The present invention comprises thermal treatment devices comprising inductive or ohmic heating elements and methods for making and using such devices. In general, the devices of the present invention comprise one or more microheaters, such microheaters can be provided to a barrier and when activated by particular frequencies, the microheater causes thermal treatment to remove an area of the barrier next to or near the end tip of a microheater. The device may comprise a unitary device comprising an energy supply component and a microheater component, comprising one or more microheaters, where the energy supply component and the microheater component are electrically connected by a wire or other means. Alternatively, the thermal treatment device may comprise a dual component device comprising two separate components, an energy supply component, and a component comprising one or more microheaters, which is referred to as the microheater component. The thermal treatment device may further comprise, but are not limited to, microneedles, analyte sensing or retrieval components, fluid sampling components, cooling components, or transdermal active agent delivery components, patches for delivery of active agents, each of which may be incorporated into either device, the unitary device or the dual component device.

In the thermal treatment device, the microheaters may be activated by an ohmic heating element which has a high resistance point, or can be heated by inductive heating methods wherein the energy supply component supplies a modulated alternating magnetic field from an excitation coil that produces eddy currents in the microheaters or in a structure attached to the microheaters, which causes the microheaters to increase in heat due to internal ohmic loss. An aspect of the invention comprises an energy source component that is separate from and not physically connected to the component comprising the microheaters. An energy supply component comprises a basic induction power source which provides a required power output at a required power frequency, and an induction coil assembly. In general, an AC power supply sends alternating current through the coil, generating a magnetic field. When the microheaters are within the magnetic field, the magnetic field induces eddy currents in the microheaters, generating known amounts of localized heat without physical contact between the microheater and the energy source. As used herein, activated means that the microheaters are heated by either ohmic heating element methods or by inductive heating methods.

The microheaters of the present invention can be made from one or more materials that function to heat by ohmic or induction heating. An aspect of the invention comprises microheaters that function to heat by induction heating and may comprise metallic, nonmetallic or ceramic materials that provide heat when placed with the magnetic field of an induction coil. Magnetic materials resist the rapidly changing magnetic filed within the induction coil and the resulting friction creates heat, hysteresis heating, in addition to eddy current heating. A metal which offers high resistance is said to have high magnetic permeability. In most metals, eddy current loss is the dominant source of induction heating. When a conductive material experiences alternating magnetic flux inside it, an electromotive force is induced in the material that causes a circulating current or eddy current, in accordance with Faraday's law of induction. This eddy current is converted into heat due to the Joule effect (i.e, resistive loss) in the conductive material.

Microheaters of the present invention that are heated with inductive heating may be made from materials having a high relative magnetic permeability, and includes materials having a permeability from from a few tens to a few thousands. Additionally, microheaters of the present invention may comprise one or more materials having one or more Curie points. Upon reaching a set temperature, the microheater materials transition from magnetic to paramagnetic and no heating beyond the set temperature can occur. By changing the percent of constituent elements in an alloy or other material, the Curie point may be changed to a desired temperature. Devices of the present invention may comprise multiple microheaters wherein some microheaters are made from a material having one Curie point and other microheaters are made from a material having a different Curie point.

Microheaters of the present invention may also be characterized by the response to one or more frequencies of the alternating magnetic field. For example, in many cases, as the frequency is increased the amount of energy dissipated in the material and therefore, the heating rate, is also increased. The microheaters of the present invention may comprise one or more materials or geometries that are differently affected by one or more frequencies of the alternating current. This can be achieved for example, by making microheaters of differing electrical conductivities, magnetic permeabilities, coercivities, Curie temperatures, or even geometry, e.g., through the use of magnetic laminations. For example, one portion of the microheater heats to its maximum at one range of frequencies, while another portion of the microheater heats to its maximum at a different range of frequencies. Multiples of the microheaters of the present invention may comprise some microheaters that heat to the maximum heat at one range of frequencies, while different microheaters heat to the maximum heat at a different range of frequencies. Frequencies used in the present invention are from about 50 Hz to 1 MHz with high permeability materials and are in a microwave range, from about 1 MHz to about 300 GHz with good electrical conductors and extended to all ranges in between. The present invention comprises microheaters that comprise materials that are heated by methods of frequency selective heating and may also comprise materials that have temperature dependent permeability.

An aspect of the invention comprises the distance between the power supply component and the microheater component. Using ohmic heating, the power supply is in electrical wire connection with the microheater component. Using inductive heating, the power supply component is not electrically connected, through wires, to the microheater component, but may be placed in physical contact with the microheater component if necessary. The distance between the power supply component and the microheater component relates to the coupling efficiency, which is the proportional relationship between the amount of current flow in the microheaters and the distance between the microheaters and the coil. Close coupling generally increases the flow of current and thus, increases the amount of heat produced in the microheater. The power supply component may be a distance from the microheater component of from physical contact to inches to feet apart. The power supply may be manually operated or may be operated by a controller, either remote to the power supply component or may be a component of the power supply. Manual or computer software means may be used to turn the power on or off, change the frequency or provide a sweep or step up of frequencies to affect the microheater component.

A microheater of the present invention comprises a thermal member comprising a base end and a tip end. The tip end is intended to contact the barrier directly or to contact ablation materials present on the barrier. The base end of the microheater is the end opposite from the tip end, and in certain fabrication methods, may form an integral part of the array structure that connects an array of microheaters. The base end may be in contact with insulation materials, with a transdermal patch, or with analyte detecting means. Microheaters of the present invention may be made from one or more materials that are capable of being heated and transferring the heat to the surrounding environment. The thermal member may be made from a single type of metal, layers of metals, conductive oxides, conductive polymers or alloys, and include, but are not limited to, nickel, nickel-iron, ferromagnetic materials, copper, NiCu, PdCo, gadolinium-silicon-germanium alloy, aluminum, ceramic materials, electrodeposited or vapor-deposited gold, platinum, or palladium outer layer coating of nickel, nickel-iron or a magnetic stainless steel-type alloy (e.g. 400-series), indium tin oxide, lanthanum strontium cobalt oxide, and aluminum doped zinc oxide. The microheater may open or enclosed spaces, in that there is a space between portions of the thermal member or between two adjacent thermal members, or the thermal member may be a shell structure, enclosed but having a hollow interior space. For example, the loop shape of FIG. 2d is an example of an open spaced microheater with space between portions of the thermal member, and the hollow post microheater of FIG. 3 is an example of a space between two adjacent thermal members. Such spaces may or may not be used to contain ablation materials. As used herein, microheaters of the present invention may or may not be in physical contact with rapid volume change materials. Such physical contact may be by coating, applying or in some way associating the tip end, or an open or enclosed space of a microheater with one or more rapid volume change materials.

Microheater components or individual microheaters of the present invention may also comprise an insulating portion. The insulating portion acts as an insulator and prevents the transfer of heat from the heated portion of a microheater or from one or more microheaters. The insulator can be made of any material that provides thermal insulation, and is generally a nonconductor or nonmagnetic. Insulators of the present invention include, but are not limited to, Mylar, Kapton (polyimide), polyurethane, liquid crystal polymer, and epoxy.

Multiples of individual microheaters may be used. As used herein, multiples of microheaters means more than one microheater used in a microheater component. Each microheater is a separate element and thus, can be positioned at any location. The multiples of microheaters may be arranged in any desired pattern or array in or on the microheater component. The multiples of microheaters may be arranged such that microheaters having the same characteristics, such as heating frequency or Curie point, are arranged together to provide an area of the microheater component that heats under one set of conditions, and another area of the microheater component comprises microheaters having a different characteristic so that in operation, one area under one set of conditions would heat and another area would not. The multiples of microheaters may be arranged so that microheaters having one characteristic are alternated with microheaters having a different characteristic, such as heating frequency or Curie point. The microheaters may be in contact with one another by a structure such as a plate attached to the base ends of the microheaters, or by wires, or in contact within a specific group of microheaters, or may be a stand alone microheater. The activation of one or more microheaters may comprise heating the plate or other structure attached to one or more microheaters in addition to activating the microheaters.

The microheaters may be made in any shape desired for the specific application. Microheaters can be designed with different materials and geometries to produce different thermal responses. For example, the shape of the microheaters may be a disk, a cone, a donut or loop, or other geometries, and the size can vary from less than 1 micron to hundreds of microns. Other shapes contemplated are shown in the figures herein, including FIGS. 2a-e and FIG. 3. FIG. 1a-c show diagrams of thermal treatment devices of the present invention comprising an ohmic energy supply component in electrical connection with microheaters of various shapes. FIGS. 1a-c show 10 the power supply, 20 an electrical resistance microheater, and 30 an in-plane substrate, 40 a three dimensional substrate, 50 microneedle microheaters.

The energy supply component and the microheater component may be used in various applications where thermal treatment, such as to alter barrier permeability or to form micropores in a barrier is needed or desired. For example, thermal treatment to form micropores in a covering or barrier of a living organism allows for transdermal delivery of active agents into humans, animals, or plants. The thermal treatment devices may be used to provide thermal treatment to form micropores to any barrier of a living organisms, including outer barriers such as skin or mucous membranes, or inner coverings such as linings, membranes, or organ surfaces. Thermal treatments can increase barrier permeability, such as provide micropores, that are used in transport of active agents into an organism or micropores and treated sites can provide for retrieval of fluids contained by or within the barrier, and/or for detection or measurement of analytes. Examples of transdermal transport across outer skin surfaces of animals are discussed herein, but the invention contemplates other applications of transport in animals and plants, and includes industrial uses and other applications of the present devices. As used herein, thermal treatment comprises using activated microheaters or activated microheaters in combination with ablation materials to increase the permeability of a barrier, for example by forming micropores in a barrier.

An aspect of the present invention comprises a wireless induction heating device for generating micron-scale pores in the skin of a human or animal to increase the permeability of the skin, and provide active agents through the micropores using conventional transdermal patch delivery methods. The separation of the power supply component and the microheater component provides design flexibility and allows for integration of microheaters into transdermal patches. FIG. 3 shows a schematic diagram of the inductive heating system, including a power supply component comprising an AC power source 170 and an excitation (induction) coil 140, and a microheater component comprising microheaters. The wireless energizing of a magnetic field is indicated as 120, the base plate structure of the microheater 150 is attached to the hollow posts 130, and PDMS 160 provides insulation for the microheater. 190 is the barrier, such as stratum corneum, and 180 is the micropore formed in the barrier. In general, a power supply component comprises an excitation coil, a radiofrequency generator and amplifier and control logic. The microheaters are separate from the power supply component and are adjacent to a barrier, in this case, the stratum corneum of human or animal skin.

The thermal treatment devices of the present invention are used to decrease the barrier properties of a barrier, by for example, creating micropores in a barrier. The microheaters of the devices create pores with small pore size, from sub-micron to micron sized pores, and can be used to control the micropore geometry. When used to create micropores in barriers such as skin, the reduction in pore size aids in minimizing infection and pain. The devices of the present invention increase the integration density of microheaters by increasing the number microheating spots in the unit area treated by adopting advanced microelectromechanical systems (MEMS). The devices of the present invention may increase skin contact by fabricating the microheaters on the top of 3-dimensional structure with MEMS technologies. The present invention may use microneedle structures as microheaters, which may aid in control of the depth of the ablated area, or the devices of the present invention may be used to create micropores into which microneedles are inserted. For example, micropores are formed using the devices of the present invention as a pretreatment step for removing barriers, for example stratum corneum, having a high Young's modulus. The thermal treatment devices of the present invention may be used as pretreatment devices for any application where reduction in the barrier properties of a barrier, or where increased permeation of the barrier is desired. For example, the thermal treatment devices of the present invention may be used to increase the permeability of a barrier, for example, by forming micropores in a site on a barrier, referred to as the pretreatment site, and a patch comprising active agents may be applied to the pretreated site for transfer of the active agents through the pretreated site of the barrier. Additionally, the thermal treatment devices of the present invention may be used to increase the permeability of a barrier, for example, by forming micropores in a site on a barrier, referred to as the pretreatment site, and fluids, either leaking into the micropore or in the barrier, or on the opposite side of the barrier, may be sampled, or analytes in the fluid may be monitored, detected or analyzed.

The microheaters of the present invention may form micropores that are of any desired size, from less than 1 micron to a few hundred microns, and size is dependent on the size of the surface of the microheater that is in contact with the barrier. The microheaters may be heated to desired temperatures that create micropores in a barrier, such temperatures ranging from a cooled temperature, room temperature, or an unheated state, to over 400° C., or any temperature necessary to raise the ablation materials on a barrier to a temperature at which the ablation of the barrier occurs and the micropore is formed. For example, when the barrier is stratum corneum of a human, the temperature of the area of the skin in contact with the surface of the microheater is elevated to greater than 100° C.

FIG. 2a-e show examples of thermal treatment devices of the present invention wherein the microheaters are activated by inductive heating power supply component. FIG. 2a-e show diagrams of thermal treatment devices comprising a power supply component that is not connected to the microheater component and which activates the microheaters by inductive heating. FIG. 2a shows 30 in-plane substrate, 80 microheater and 70 the magnetic field produced by the power supply component. FIG. 2b shows 40 a three dimensional substrate, and 70 and 80 as above. FIG. 2c shows 60 microneedle microheaters, and 30 and 70 as above. FIG. 2d shows 100 a loop microheater, and 30 and 70 as above. FIG. 2e shows 110 hollow pointed tip post microheaters and 30 and 70 as above. An aspect of the invention comprises positioning the microheaters on an insulating substrate, on or in a transdermal patch, and the microheaters are activated by a separate inductive power supply component unit. Tests have shown that with microheaters activated by inductive heating, the temperature of a microheater surface increases along with the induction time, and the tip end of the microheater metal shell shows a faster heating response than does the basement or side walls of the metal shell of the microheater.

Examples of microheaters for use with inductive heating power supply components of the present invention include a metallic cone structure of tip diameter of 80 µm, base diameter of 400 µm, metal shell thickness of 50 µm, and height of 2 mm; and an array of hollow metallic posts, with an inner tip diameter of 100 µm, metal thickness of 30 µm, and post height of 400 µm. Fabrication of the metallic cone structure included laser drilling polymer sheets to form molds containing conically tapered holes, then electrodepositing a thin conductive metal seed layer onto the mold, and electroplating nickel onto the mold to form the final shell cone-shaped structures. Only the small tip area is intended to contact the barrier, thus providing a small, controlled porated area of the barrier.

The hollow metal cone shaped microheaters were characterized to assess their electrical performance. According to well-established inductive heating theory, the inductive heating power of the heating elements is represented as an AC resistance, i.e., the real part of the impedance, of the excitation coil. Therefore, by measuring the portion of the AC resistance of the excitation coil attributable to the heating elements, the heating power delivered to the heating elements can be estimated.

Figure 4:
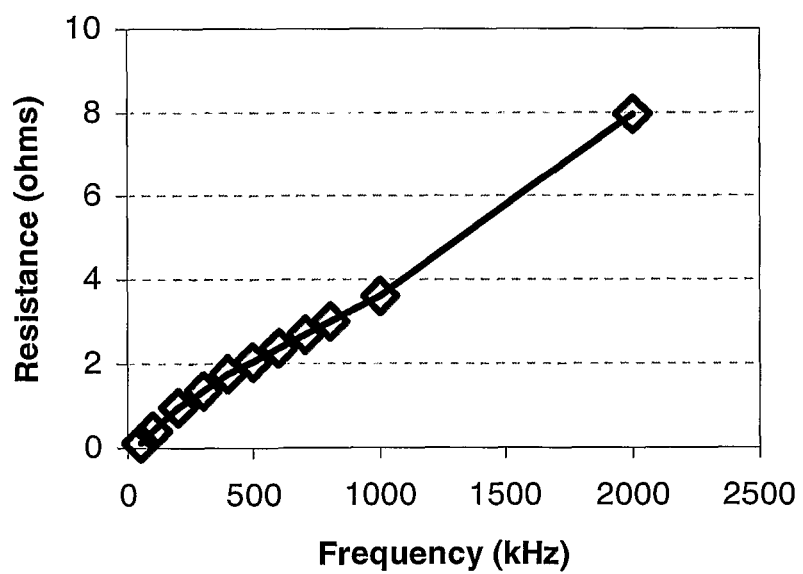
FIG. 4 is a graph of the electrical resistance of the inductive heating element, $R_{IH}$, over a frequency range of 50 kHz-2 MHz.

The AC resistance of the inductive heating system ($R_{IH}$) is calculated as the difference between the resistance of the excitation coil with the heating element inside and the resistance of the excitation coil without the heating element inside. The AC resistance of the excitation coil both with and without the heating elements inside was measured and the $R_{IH}$ was calculated. FIG. 4 indicates that $R_{IH}$ increases with increasing frequency, indicating that heating power also increases with increasing frequency even though the input current of the excitation coil remains the same. The inductive heating power of this system was then determined as $(I_{input})^2 R_{IH}$. Using data in FIG. 4 shows that when the input current to the coil is 1 A (Amp), the resultant heating power on the hollow cone is approximately 1 W (watt) and 8 W at 200 kHz and 2 MHz, respectively.

To characterize the thermal output of inductive microheaters, the temporal evolution of the surface temperature of hollow metal cones was measured after an excitation pulse using an infrared camera with spatial resolution of 5 µm. The IR camera image displayed the surface temperature distribution and indicated a large temperature increase up to 132° C. on two microheaters imaged. These results are for a highly non-optimized inductive heating system. With optimization of components, different results are seen.

Figure 5:
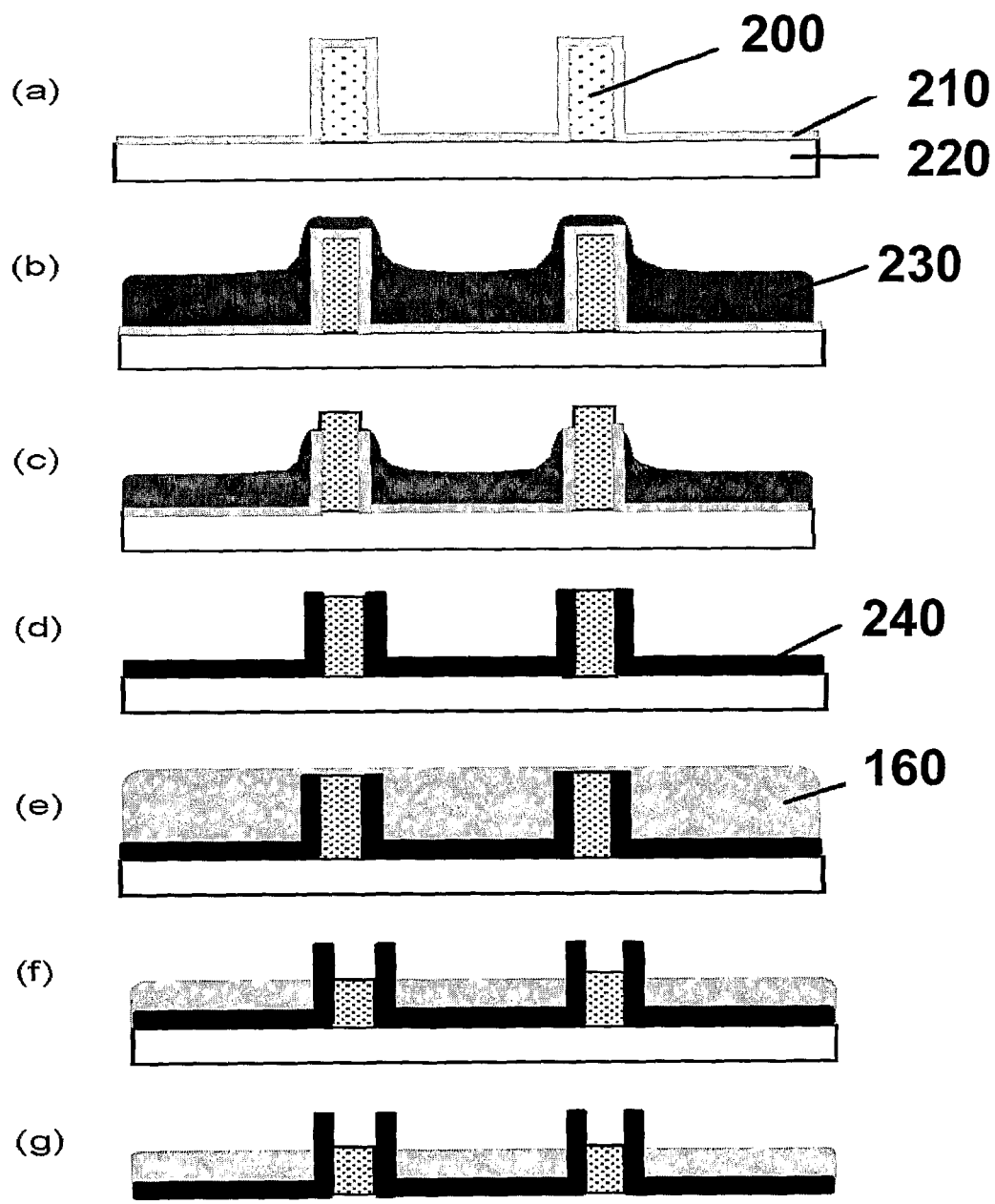
FIG. 5a-g are a schematic of the fabrication of a microheater.

An example of methods for fabrication of a post type microheater is shown in FIG. 5. In general, microheaters can be fabricated using micromachining techniques by a process which consists of first patterning the shape of the structures onto a polymer mold using lithography and then electroplating metal into the mold to generate the metal heating elements. Using such methods, microheaters with dimensions from 1 µm to 1 mm can be made. FIG. 5a-g shows steps for making a microheater of the present invention. Photosensitive or photopatternable epoxy polymer SU8 (Microchem, Inc.) 200 is patterned to form an array of posts on a dummy substrate (glass) 220 and an electroplating seed layer of Ti/Cu 210 is deposited on it. (5a) Polymethylmethacrylate (PMMA) 230 is applied to the posts (5b). Reactive ion etching (RIE) is performed to expose the top portion of the posts, and the exposed seed layer is removed by wet-etching (5c). The remaining PMMA is removed by an organic solvent rinse. Nickel 240 is electroplated on the seed layer, and the protruding SU8 is polished away (5d). Polydimethylsiloxane (PDMS) 160 is applied evenly to the structure (5e). Again, RIE is performed to reveal the tip of the electroplated posts (5f). Finally the entire microheater array is released from the dummy substrate (5g). The microheater array was formed as a 20×20 array of hollow posts with a base plate. The base plate in this array forms a connection between all of the microheaters, and when exposed to the power supply component and is activated, generates the induction (eddy current) heat and transfers the heat to the hollow posts. The PDMS layer provides an insulation layer between the base plate and the barrier. When the microheater component is heated, there is no transfer of heat from the base plate to the barrier, and the only heat transferred to the barrier is, in this example, at the tip end of hollow posts of the microheater. The hollow posts can be made of nickel, which has a high relative magnetic permeability.

Power supply components may be made by techniques known to those skilled in the art. For example, the excitation coil can be fabricated by conventionally winding conductor coils on optimally-shaped hollow polymer cores, optionally incorporating flux-guiding magnetic material. Size, frequency and coil current can be optimized for the particular application.

Figure 6:
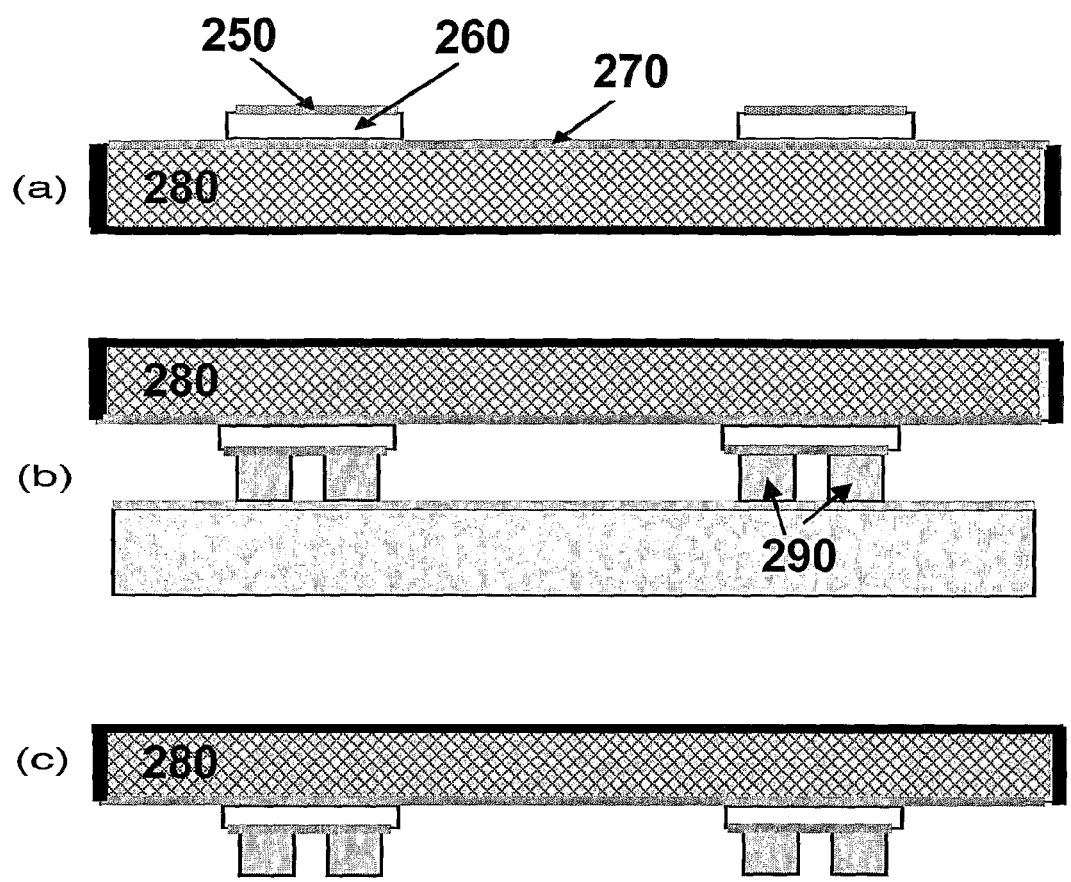
FIGS. 6 a-d is a schematic of the fabrication of a transdermal patch incorporating microheaters on the surface.
Figure 7:
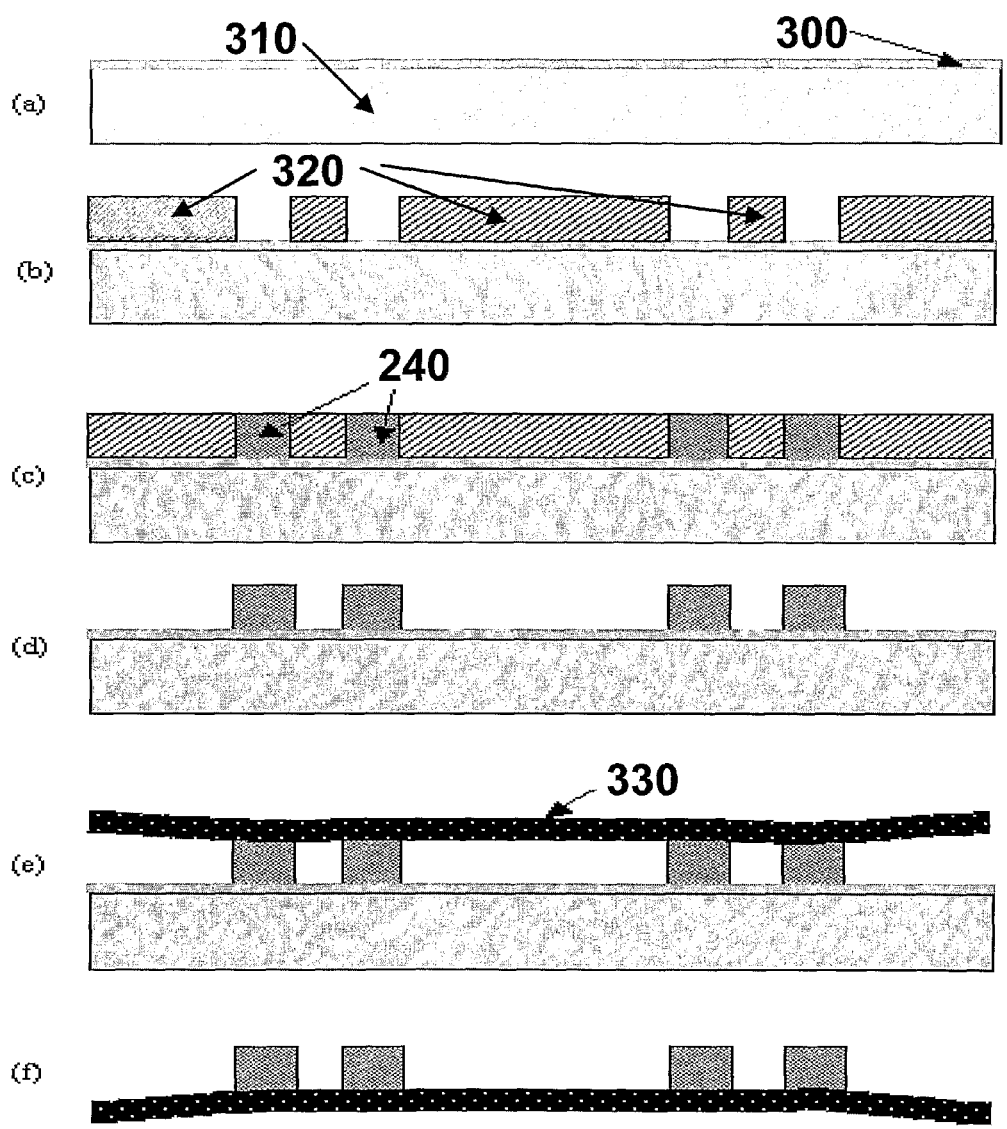
FIG. 7a-f is a schematic of the fabrication of the microheaters and attachment to a polymer backing.
Figure 8:
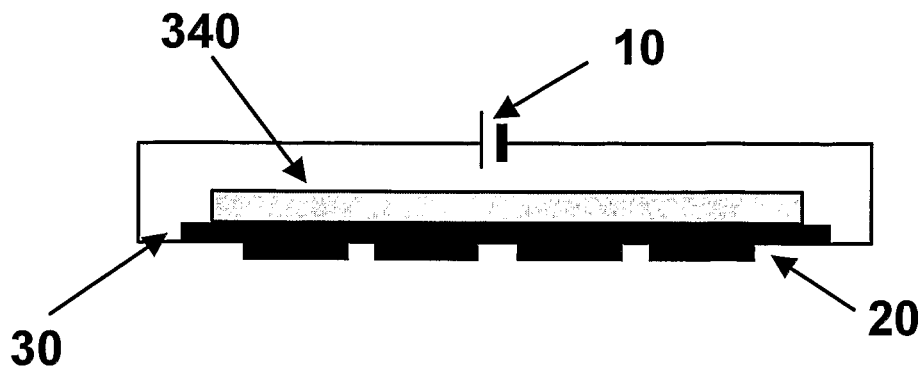
FIG. 8 is a profile diagram of a thermal treatment device comprising a cooling element.

The present invention comprises a transdermal drug delivery device comprising a power supply component and a microheater component comprising a transdermal patch comprising at least one active agent and one or more microheaters in an array. The microheater component is an integral to the transdermal patch such that when the microheaters are heated, the barrier, such as skin or membrane of a human or animal, that the microheaters are touching is ablated, and the active agent of the transdermal patch enters the micropore in the barrier and transits the barrier, such as entering the human or animal through the micropores that are formed. A fabrication method for the transdermal drug delivery device is shown in FIGS. 6a-c, and also in greater detail in FIG. 7a-f. FIG. 6a shows an adhesive layer 250 in contact with an insulating layer 260 such as a polyester Mylar, in contact with an adhesive layer 270 all of which are attached to a patch 280 with an active agent contained within the body of the patch. FIG. 6b shows the attachment of microheater 290 to the adhesive layer 250 of the patch. FIG. 6c shows the microheater component comprising a patch, such as a transdermal patch, and microheaters disposed on an outer surface. FIGS. 7a-f show fabrication steps for a microheater component comprising a polymeric patch and microheaters. FIG. 7a shows a glass substrate 310 with an electroplated seed layer of gold or nickel 300 using a vacuum deposition process. FIG. 7b shows photoresist 320 patterned on the seed layer. The metallic microheater array 240 is electroplated through the photoresist mold, as shown in FIG. 7c. FIG. 7d shows the photoresist removed with acetone. A polymer patch 330 with adhesive is allied to the electroplated microheater array on the glass, see FIG. 7e, and the array is released from the substrate in FIG. 7f. A transdermal patch, such as those known in the art, containing the active agent is covered with an impermeable polymer layer, which does not transfer active agents, on the back and sides, of the transdermal patch. The transferring surface has an adhesive layer, generally for attaching the patch to a recipient. Pre-cut polyester, such as Mylar, with a thickness of 100 µm is placed on the adhesive layer. Mylar is an example of a thermally insulating material that provides good thermal isolation with a relatively thin layer. Microheaters are aligned and transferred to the transdermal patch by adhesive onto the Mylar layer, resulting in an integrated transdermal patch comprising microheaters. Pores in the insulating layer may be used to allow for movement of the active agent contained in the transdermal patch from the patch to the skin. Alternatively, the Mylar may be present as an insulator only at the contact area with the base end individual microheaters.

Transdermal patches are well known in the art and the present invention includes all forms of transdermal delivery of active agents comprising an incorporated microheater component including, but not limited to, transdermal devices such as devices with a fill and seal laminate structures, peripheral adhesive laminate structures and solid state adhesive laminate structure or devices with the active agent incorporated in the adhesive. As used herein, a patch functions in the same manner as a transdermal patch, but a patch can be used on any barrier to supply compositions such as active agents to the barrier, but is not limited to epidermis or dermis of human or animal skin as the barrier, as may be understood for transdermal patch. Transdermal drug delivery is discussed in general in Cleary, G. W., "Transdermal Drug Delivery", Cosmetics & Toiletries, Vol. 106, pgs. 97-109, 1991 which is incorporated herein by reference. Transdermal devices for the delivery of a wide variety of biologically active agents have been known for some time and representative systems which utilize rate controlling membranes and in-line adhesives are disclosed in U.S. Pat. Nos. 3,598,122; 3,598,123; 3,742,951; 4,031,894, 4,144,317; 4,201,211 and 4,379,454 which are incorporated herein by reference. Such devices generally comprise an impermeable backing, a drug or active agent reservoir, a rate controlling membrane and a contact adhesive layer which can be laminated or heat sealed together to produce a transdermal delivery device. U.S. Pat. Nos. 5,013,293; 5,312,325 and 5,372,579 disclose an electrolytic transdermal patch provided with a current oscillator for the periodic delivery of an active agent, and are herein incorporated by reference. Other methods for control of transport are taught in Smith, et al. 1995, and Bronaugh, et al., 1999. The driving force for transport may include gradients in concentration, chemical potential, pressure, osmotic pressure, voltage and other gradients. Methods may include diffusion, osmosis, convection, electrophoresis, electrosmosis, convective dispersion and other mechanisms. As shown herein, these and other transdermal delivery devices can incorporate one or more microheaters for thermal treatment of the skin to aid in the transdermal flux rate of the active agent and reduce the barrier properties of the skin or other membranes.

As used herein active agent means a pharmaceutical or biotechnological compound or construct that induces a biological or pharmacological effect on an organism; and can also be a compound, molecule, chemical, or biological construct, that provides a physical or chemical change to an existing condition.

The methods and devices of the present invention allow for the delivery of active agents that may or may not currently be delivered using transdermal delivery patches. The delivery of many agents are limited by the barrier functions of skin or membranes of organisms. Active agents of the present invention include, but are not limited to, agents for gene therapy, nucleic acids, viruses, antigens, immunogens, chemical or biological materials or compounds that induce a desired biological or pharmacological effect, antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, progesterone and derivatives, testosterone and derivatives, including corticosteroids; angiogenic agents, antiangeogenic agents, hypnotics; immunosuppressives; muscle relaxants; parasympatholytics; nicotine, psychostimulants; sedatives; tranquilizers, ionized and nonionized active agents, and compounds of either high or low molecular weight. The active agents may have local effects, such as providing for a local anethesia, or may have systemic effects. The present invention is contemplates the mode of delivery of active agents, and is not limited by the particular active agents delivered. Other methods for increasing transport of molecules across skin or other membranes may be used with the present invention such as microneedles, ultrasonication or electroporation techniques.

Though not wishing to be bound by any particular theory, it is believed that the micropores formed by the heat delivered by the microheater to the area of the barrier immediately adjacent to or touching the tip of a microheater are formed due to the heat from the microheater causing a rapid expansion or a rapid change in volume of one or more substances present. Such substances that undergo this change in volume and aid in formation of the micropore are referred to herein as ablation material or ablation materials. Ablation material includes any liquid, gel, solutions or multiphase materials, or solid, alone, or in combination with other liquids, gels, solutions or multiphase materials or solids in chemical mixtures or reactions, that, in response to the heat provided by the microheater, undergoes a volume expansion, in 1 microsecond to 1 second, that is sufficiently extensive to physically remove at least a portion of the barrier. Ablation materials having vaporization temperatures, as in those materials that vaporize at temperatures, of from about 24° C. to about 200° C. are useful. Ablation materials may be in physical contact with a microheater, or may be provided in a separate composition to a barrier.

Alternatively, the microheaters of the present invention may alter or decrease the barrier properties of the barrier, or increase the permeability of the barrier, by heating effects on materials present. For example, heating of the skin may liquefy oils or fats in the skin to alter the barrier properties of the skin. The present invention comprises methods of providing ablation materials to the environment to ablate sites, or form micropores, in a barrier site adjacent to or touching the tips of microheaters. Such ablation materials may be provided to the barrier prior to application of the microheater component to the barrier, may be provided simultaneously with application of the microheater component to the barrier, or may be physically associated with the microheater component or the individual microheaters. For example, solutions, multiphase liquids or gels comprising ablation materials may be provided to the barrier prior to the application of the microheater component to the barrier. Upon heating of the microheaters, the liquid or gel, or ablation materials comprised by the liquid or gel, are affected by the temperature of the microheaters, undergo a rapid volume change, the barrier is affected and at least one micropore is formed in the barrier. Another example of providing ablation materials comprises providing hydrated salts, for example, coated on the tip ends of the microheaters or coated within a hollow portion of a microheater, and when the microheater is heated, the solid is affected by the temperature of the microheater, undergoes a rapid volume change, the barrier is affected and the micropore is formed in the barrier. Compounds or chemical mixtures that participate in chemical reactions to undergo rapid volume changes in response to the heat from the microheater may be provided to the barrier through these methods and provide ablation materials for affecting the barrier and forming the micropore in the barrier when the microheater is heated. Such compounds or chemical mixtures may be provided directly to the barrier or associated on or within a hollow portion of a microheater. For example, ablation materials may be in a solid form and found within a hollow portion of microheaters such as those shown in FIGS. 2*d-e*, and 10. Examples of such ablation materials include, but are not limited to, ablation materials comprise liquids, gels or solids, comprising hydrophobic liquids, hydrophilic liquids, water, ethanol, methanol, organic compounds, alcohols, ketones, aldehydes, amines, ethers, esters, oils, paraffins, fatty acids, salt hydrates, including but not limited to calcium hydrates, sodium sulphate decahydrate, sodium phosphate dodecahydrate, calcium chloride hexahydrate and sodium thiosulfate pentahydrate, mixtures or combinations. Poration of the barrier may also be accomplished by affecting the barrier by contacting a selected area, up to about 1000 μm across, of the barrier with a microheater such that at least some of the temperatures of localized ablation materials, such as tissue-bound water, oils, sebum, cellular debris, and other substances in the selected area are heated to a point where one or more of the substances undergoes a rapid volume change and the selected area of the barrier is affected, and a micropore is formed.

As used herein "poration," "microporation," or a similar term means the formation of a small hole or pore in a barrier in a selected area of the barrier which lessens the barrier properties of the barrier to the passage of analytes from the side of the barrier opposite from where the microheaters are contacting the barrier, for detection or measurement of analytes, or the passage of active agents across the barrier. Micropores formed are generally no larger than about 1 mm in diameter, and more preferably no larger than about 100 μm in diameter, and will extend as far into the barrier as desired, but at least to a depth where the barrier properties of the barrier are disturbed, without adversely affecting underlying or nearby structures.

As used herein "ablation" means the controlled removal of an area of the barrier, due to the actions of the ablation materials and the activated microheater, or the activated microheater alone contacting the barrier at the selected site. Though not wishing to be bound by any particular theory, it is believed that the heat provided by the microheaters, optionally in combination with added ablation materials, leads to the barrier or components of the barrier to be rapidly expelled from the contact site.

Methods of the present invention comprising increasing the transdermal flux rate of an active agent across a barrier, such as the skin or membranes of an organism, comprise using the devices described herein to increase the permeability of the barrier by applying a microheater component to a barrier, activating the microheaters in the microheater component, porating the barrier by forming one or more micropores in specific sites in the barrier without causing widespread damage to the barrier or underlying structures, reducing the barrier properties of the barrier to the transdermal flux rate of the active agent; while contacting the porated specific area with a composition comprising an effective amount of the active agent such that the transdermal flux rate of the active agent into the body is increased. For example, methods of the present invention comprise increasing the transdermal flux rate of an active agent across the stratum corneum of a human or animal, comprising using a thermal treatment device comprising a power supply component that is not physically connected to a microheater component, and a microheater component comprising a transdermal patch wherein one or more microheaters are present on or in one surface of the transdermal patch such that application of the transdermal patch to the stratum corneum of a human or animal brings the microheaters in contact with the stratum corneum, activating the microheaters, increasing the permeability of the stratum corneum by porating the stratum corneum by forming one or more micropores in specific sites in the stratum corneum without causing widespread damage to the stratum corneum or underlying dermal layers, reducing the barrier properties of the stratum corneum to the transdermal flux rate of the active agent; and providing the porated stratum corneum with a composition comprising an effective amount of the active agent such that the transdermal flux rate of the active agent into the body is increased.

As used herein, "transdermal flux rate" is the rate of passage of any analyte from one area or surface of a barrier to another area or surface, or the rate of passage of any active agent from one area or surface of a barrier to another area or surface. This term is commonly understood by those skilled in the art, and its usual and customary meaning is intended herein. As used herein, "analyte" means any chemical or biological material or compound which may be measured, determined, monitored, and/or analyzed in order to gain information, or determine the status, related to the object or organism that is the source of the analyte. Glucose is an example of an analyte, and other examples of analytes include, but are not limited to, sodium, potassium, bilirubin, urea, ammonia, calcium, lead, iron, lithium, salicylates, hormones, and the like.

Optionally, the methods of the present invention may be preceded or followed by methods for cooling the area of the barrier, such that the methods may further comprise cooling the selected area of barrier and adjacent areas with cooling means such that said selected area and adjacent areas are in a selected precooled, steady state, condition prior to poration. An example of incorporation of a cooling component is seen in FIG. 8. FIG. 8 is a diagram of a thermal treatment device with a power supply 10, a Peltier cooler 340, in combination with the in-plane substrate 30, and microheaters 20.

Methods of the present invention comprise thermal treatment of a barrier with the devices described herein such that interstitial fluid, other bodily fluids, or fluids retained by the barrier, exudes from or forms in the micropores, collecting or sampling the fluid in the micropore, and analyzing, measuring or detecting, one or more analytes in the collected fluid. Collecting or sampling means include, but are not limited to, a vacuum or absorption member, may be applied to the microporated area to remove the fluids. Alternatively, the fluid and any analytes therein may be analyzed, measured or detected in situ in the micropore, without removal of the fluids. Methods for determining or measuring analytes are known in the art, and include, but are not limited to color change assays, immunoassays, specific binding partner assays, and other tests for analytes. Following such analysis, measurement or detection methods, one or more micropores can be sealed by reactivating the microheater using the power supply component to cause fluid remaining in the micropore to coagulate. Alternatively, the devices of the present invention can be used to reopen pores that begin to close by reactivating the microheaters. These reactivations are accomplished by providing the energy supply component within a range of distance to the microheaters so as to activate the microheaters.

The methods of the present invention contemplate that microheater components may be applied, stuck by adhesives, attached, bound, wrapped within a dressing, or by other means of attaching the component, for a limited time period to a barrier. For example a transdermal patch microheater component may be applied the skin or membranes of a human or animal for 0.5 minutes to 24 hours, for 1-6 days, for 1-3 weeks, for months at a time. Other microheater components may be applied to a barrier for longer periods, depending on the intended uses. The individual microheaters in the microheater components of the present invention may be activated once to provide heat transfer to specific sites on the barrier or may be activated multiple times, including from 1 to 1000 times, from 1-20 times, from 5 to 50 times, and all times in between. The microheater component may remain in the same site on the barrier or may be moved to different sites, depending on the intended use. The present invention contemplates one or more activations of a microheater to form and/or maintain micropores. For example, one activation of a microheater, comprises heating the microheater to its predetermined temperature, and allowing it to return to a cooler temperature or to a preactivation temperature. Such activation may be accomplished by a power supply component providing ohmic heating or a power supply component providing inductive heating. The activation of the microheater may further comprise the actions of ablation materials present on the barrier or physically contacting the microheater in response to the heat from the microheater. To form a micropore with the diameter and depth desired for a particular intended use, one or more activations may be necessary, and is also dependent on the barrier properties of the barrier.

An aspect of the present invention contemplates microheater components that are activated one or more times by a handheld power supply component, disposing of the first microheater component and replacing it with a second microheater component which can then be activated by the original handheld power supply component. The present invention alters the way drugs are delivered. Given the many advantages of transdermal patch delivery—e.g., control of drug delivery rate, self-administration, non-invasive delivery, high patient compliance—the devices and methods of the present invention can, in many cases, replace hypodermic needles currently used to inject drugs, and is especially useful for delivery of proteins, nucleic acids and other biotechnology-derived compounds. Inherent to the current invention is that the drug or active agent reservoir remains outside the body and the drug or active agent is transported into the body through micropores. This gives patients and careproviders greater flexibility to interact with and modulate the delivery device, or even remove it if needed. Moreover, the present invention has flexibility in that the materials used and their sterility are not subject to the same safety constraints as for implants, injections, or pills.

Methods and devices for creation of micropores in the skin have utility beyond drug delivery. As disclosed herein, fluid and analytes can be extracted out of the skin for minimally invasive monitoring of drugs, disease markers, glucose, and other metabolites. Micropores also provide conduits for low-resistance electrical flow for gel-free monitoring of vital signals or therapeutic electrical stimulation.

The wireless devices of the present invention also have capabilities that can impact medicine. For example, such devices provide non-invasive skin microablation using a power source isolated from the skin. The wireless heating devices and methods separate cheap and disposable microheaters from a reusable power source, thereby, providing economic, sanitary, and convenient microablation methods. Independent microheaters or arrays of microheaters embedded within a transdermal patch, can facilitate use of well-established transdermal technology and manufacturing, as well as providing a small, cosmetically acceptable device. The simplicity of the devices and methods of the present invention make use by elderly, pediatric, veterinary and other patients more straightforward.

Further, the wireless heating technology of the present invention has other applications. For example, the on-demand, wireless heating may be used to activate release of drug in a pulsatile manner, of critical importance to drugs such as hormones. The wireless nature also facilitates communication between the device and a remote microprocessor that could control device operation, which may be in conjunction with input from biosensors or other sources. Wireless activation also lends itself to controlling delivery from a device injected or implanted in the body. Drug release can be remotely controlled for spatial or temporal targeting in an actively controlled manner that is mostly non-invasive.

The present invention comprises methods, devices and systems for thermal treatments of barriers to increase the permeability of the barrier, and to reduce the barrier properties of the barrier. Thermally altering the components of the barrier or providing micropores in the barrier can increase the permeability and reduce the barrier properties of the barrier. Such thermal treatments may be used alone or as a pretreatment step, or in conjunction with other activities. In the methods, devices and systems disclosed herein, a barrier can be a solid structure interposed between two areas, and an example is a bladder, a membrane, a diaphragm, mucous membranes, organ covering membranes, outer skin, outer layers of organisms, or industrial or mechanical barriers. Thermal treatment devices useful in the methods and systems disclosed herein comprise a unitary device where the microheater component is in electrical wire connection with the power supply component, and the power supply component activates the microheater component by ohmic heating; or may be a wireless device and the microheater component is separate from the power supply component, and the power supply component activates the microheater component by inductive heating. Ablation material or materials useful in the methods, devices and systems described herein comprise liquids, gels, solutions, multiphase materials, or solids, comprising hydrophobic liquids, hydrophilic liquids, water, ethanol, methanol, organic compounds, alcohols, ketones, aldehydes, amines, ethers, esters, oils, paraffins, fatty acids, salt hydrates, including but not limited to calcium hydrates, sodium sulphate decahydrate, sodium phosphate dodecahydrate, calcium chloride hexahydrate and sodium thiosulfate pentahydrate, mixtures or combinations. Such ablation materials may or may not be present or be used in the methods, devices and systems disclosed herein. Microheaters useful in the devices, methods and systems disclosed herein comprise a disk, a cone, a donut, a hollow post, or loop, from less than 1 micron to hundreds of microns in length. The microheater may be made of a single type of metal, layers of metals, conductive oxides, conductive polymers or alloys, nickel, nickel-iron, ferromagnetic materials, copper, NiCu, PdCo, gadolinium-silicon-germanium alloy, aluminum, ceramic materials, electrodeposited or vapor-deposited gold, platinum, or palladium outer layer coating of nickel, nickel-iron, a magnetic stainless steel-type alloy, 400-series alloy, indium tin oxide, lanthanum strontium cobalt oxide, and aluminum doped zinc oxide.

A method for increasing the permeability of a barrier comprises applying an effective amount of an ablation material to a selected site on the surface of a barrier; providing a thermal treatment device comprising a microheater component comprising at least one microheater to the selected site on the surface of a barrier so that the ablation material is disposed between a tip end of the microheater and the surface of the barrier; activating the microheater component comprising at least one microheater with a power supply component; heating the ablation material to a temperature sufficient to increase the volume; and increasing the permeability of the barrier. Another method for increasing the permeability of a barrier comprises providing to a selected site on a barrier surface, a device comprising a microheater component comprising at least one microheater comprising an ablation material, activating the microheater component comprising at least one microheater comprising an ablation material with a power supply component; heating the ablation material to a temperature sufficient to increase the volume; and increasing the permeability of the barrier. A thermal treatment device of the present invention comprises a microheater component comprising at least one microheater comprising a thermal member having a base end and a tip end; an ablation material in contact with the microheater; and a power supply component for activating at least one microheater of the microheater component. A microheater of the present invention comprises a thermal member comprising a base end and a tip end; and an ablation material in physical contact with the thermal member.

The present invention comprises a method of transdermal delivery of an active agent, comprising, contacting a selected site on a surface of skin or a membrane of a human or animal with a thermal treatment device comprising a microheater component comprising at least one microheater having an ablation material in physical contact with the microheater, and a transdermal patch comprising at least one active agent; activating the microheater component comprising at least one microheater and a transdermal patch, with a power supply component so as to heat the ablation material to a temperature sufficient to increase its volume; increasing the permeability of the surface of the skin or membrane; and allowing the device to contact the barrier for a sufficient amount of time for the transfer of an effective amount of one or more active agents from the transdermal patch to the surface of the skin. Another method of transdermal delivery of an active agent comprises, contacting a selected site on the surface of skin or a membrane of a human or animal with a thermal treatment device comprising a microheater component comprising at least one microheater having an ablation material in physical contact with the microheater; activating the microheater component comprising at least one microheater, with a power supply component so as to heat the ablation material to a temperature sufficient to increase its volume; increasing the permeability of the surface of the skin; removing the microheater component; and applying a transdermal patch comprising at least one active agent to the selected site for a sufficient amount of time to transfer an effective amount of one or more active agents from the transdermal patch to the surface of the barrier. A method of delivery of an active agent across a barrier comprises contacting a selected site on the surface of a barrier with a thermal treatment device comprising a microheater component comprising at least one microheater having an ablation material in physical contact with the microheater, and a patch comprising at least one active agent; activating the microheater component comprising at least one microheater and a patch, with a power supply component so as to heat the ablation material to a temperature sufficient to increase its volume; increasing the permeability of the barrier; and allowing the device to contact the barrier for a sufficient amount of time for the transfer of an effective amount of one or more active agents from the patch to the surface of the barrier.

A method of increasing the permeability of a barrier for sampling a fluid contained by the barrier comprises contacting a selected site on the surface of a barrier with a thermal treatment device comprising a microheater component comprising at least one microheater having an ablation material in physical contact with the microheater, and a means for sampling a fluid; activating the microheater component comprising at least one microheater, with a power supply component so as to heat the ablation material to a temperature sufficient to increase its volume; increasing the permeability of the barrier; and sampling a fluid released by the barrier. A sampling or collecting method may further comprise detecting, monitoring, or analyzing an analyte in the sample, an analyte is any chemical or biological material or compound which may be measured, determined, monitored, and/or analyzed in order to gain information, or determine the status, related to the object or organism that is the source of the analyte. The present invention comprises systems comprising a system for transdermal delivery comprising, a thermal treatment device comprising a microheater component comprising at least one microheater having an ablation material in physical contact with the microheater, and a transdermal patch comprising at least one active agent; and a power supply component to activate the microheater component so as to heat the ablation material to a temperature sufficient to increase its volume.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

The hollow post type microheater was fabricated as follows. Photosensitive epoxy polymer SU8 (Microchem, Newton, Mass., USA) was patterned to form an array of posts on a dummy substrate (glass, 2"×3"×1 mm, Dow Corning, Midland, Mich., USA) and an electroplating seed layer of Ti/Cu was deposited on it using a DC sputterer (CVC DC sputterer, CVC, USA). Polymethylmethacrylate solution (PMMA, Microchem, Newton, Mass., USA) was applied to the posts. Reactive ion etching (RIE) was performed to expose the top portion of the posts using a reactive ion etcher (Plasma-Therm RIE, Plasma-Therm, ST. Petersburg, Fla., USA), and the exposed seed layer was removed by wet-etching (sulfuric acid (10 ml)+$H_2O$ (100 ml) and hydrofluoric acid (5 ml)+$H_2O$ (100 ml). The remaining PMMA was removed by an organic solvent (ethyl lactate) rinse. Nickel was electroplated on the seed layer, and the protruding SU8 was polished away. Polydimethylsiloxane (PDMS, Dow corning, Midland, Mich., USA) is applied evenly to the structure. Again, RIE was performed to reveal the tip of the electroplated posts using a reactive ion etcher (Plasma-Therm RIE, Plasma-Therm, St. Petersburg, Fla., USA). Finally the entire microheater array was released from the dummy glass substrate. The microheater array was formed as a 20×20 array of hollow posts with a base plate. Both the hollow posts and the base plate were made of electroplated nickel.

Example 2

Figure 9:
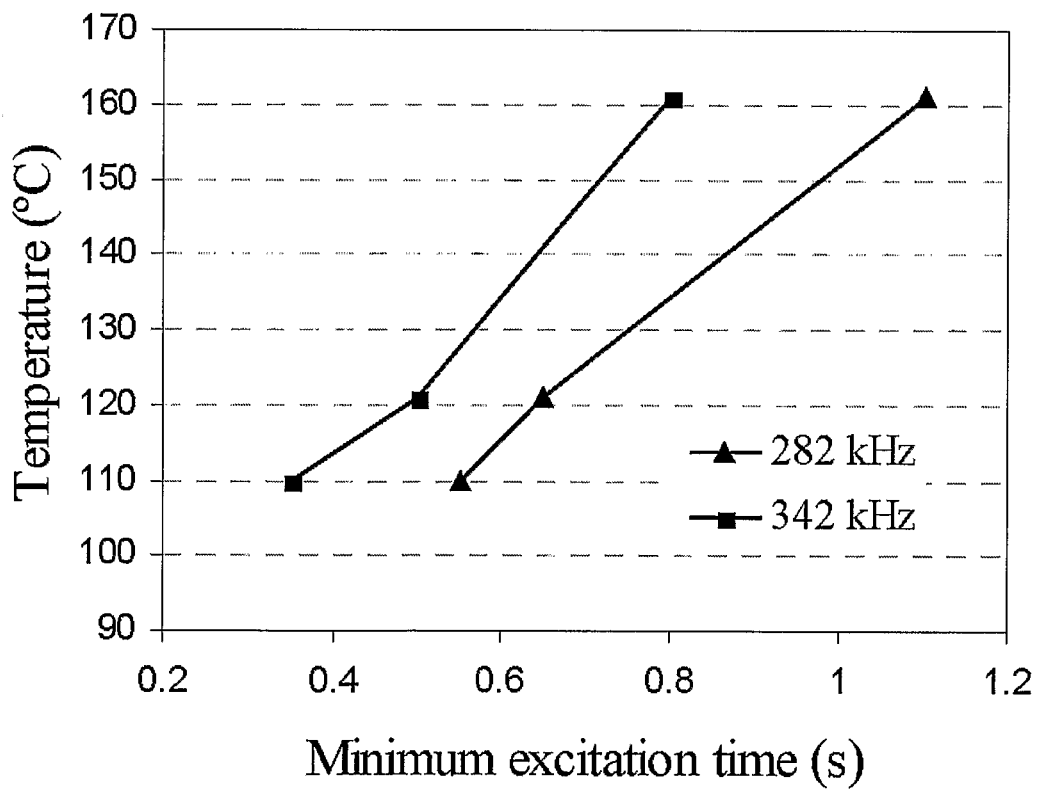
FIG. 9 is a graph showing the induction heating characteristics of a hollow post microheater array.

The induction heating performance of the fabricated hollow post array of EXAMPLE 1 has been characterized while applying an AC magnetic field with the excitation coil. Liquid crystal polymer (LCP) paper, which changes its color permanently when a temperature exceeds pre-set temperatures of 110, 121 or 161° C., was used as a temperature indicator for initial studies. The hollow post array was placed on top of the temperature indicator papers inside the coil, and an AC current of controlled duration (0.05 second increment) and specified frequency was applied to the coil. The resulting temperature data is shown in FIG. 9. The excitation time was recorded when each LCP paper changed color. Therefore, the x axis of graph represents the minimum time required to achieve the given temperature (the y axis). The RMS magnetic field applied to the heating element was approximately 50 auss at frequencies of 282 and 342 kHz. Since eddy current loss in the micro-heating element increases with applied frequency, the higher frequency excitation produced higher temperature than lower frequency as expected. It is believed that the temperature needed for thermal ablation of skin is approximately 109° C., it can be concluded that the prototype hollow post array can microablate skin. The marks on the paper mimicked the pattern of the posts, indicating the localized heat pattern representative of the ring-shaped tip of the posts.

Finite element analysis (FEA) was performed to estimate induction heating power of the microheaters from EXAMPLE 1 for the multiple frequencies, using ANSYS Emag 7.1. Three-dimensional simulation was performed for a quarter portion of the single post section. The simulation parameters and simulated results are given in Table 1.

TABLE 1

| Relative permeability of NI | 100 |
|---|---|
| Electrical resistivity of NI (Ω · m) | $0.69 \times 10^7$ |
| Average power density at 282 kHz (W/m³) | $0.37 \times 10^9$ |
| Average power density at 342 kHz (W/m³) | $0.52 \times 10^9$ |
| Average power density at 1 Mhz (W/m³) | $2.7 \times 10^9$ |

The results indicated that average power density (APD) of the 342 kHz excitation was 1.4 times larger than that of 282 kHz. Also, it was estimated that if the excitation frequency increased to 1 MHz, the APD increased to almost 5.2 times that at 342 kHz, which provides a rapid temperature response of the heating element. The rapid heat response is expected to offer a steep thermal gradient across the stratum corneum, so that any unnecessary heat effect to the viable skin could be minimized. A simulated induction power density for the cross-section of a microheater at 342 kHz indicated that non-uniform heating power generation due to the non-uniform eddy current distribution for the given geometry was present. The outer perimeter of the post generated more power than the inner perimeter.

Example 3

Figure 10:
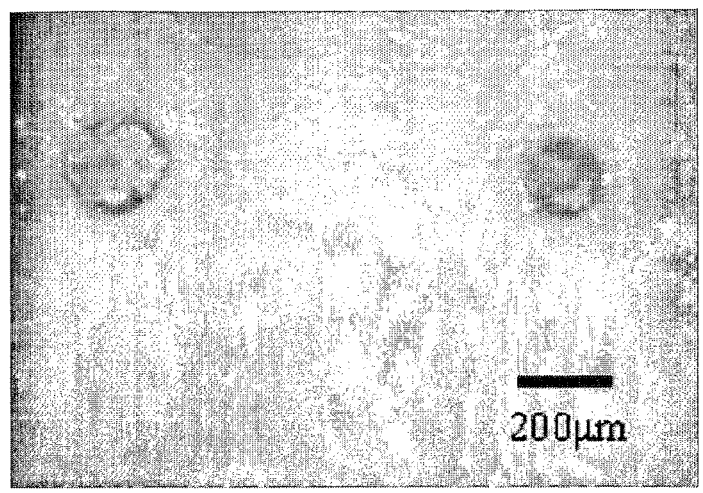
FIG. 10 is a photomicrograph of micropores formed in ablated human cadaver skin using the metallic cone-shaped microheaters.
Figure 11A:
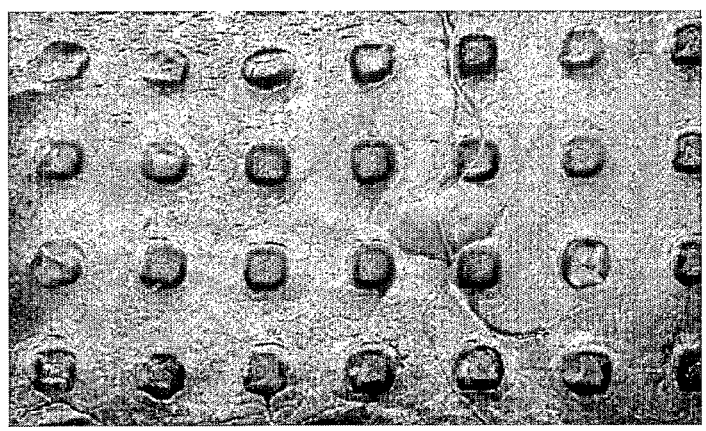
FIGS. 11a and b are scanning electronmicrographs (SEM) of micropores formed in human cadaver skin using the hollow post microheater array. (a) is a top view, and (b) is an angled view of the same tissue as (a).
Figure 11B:
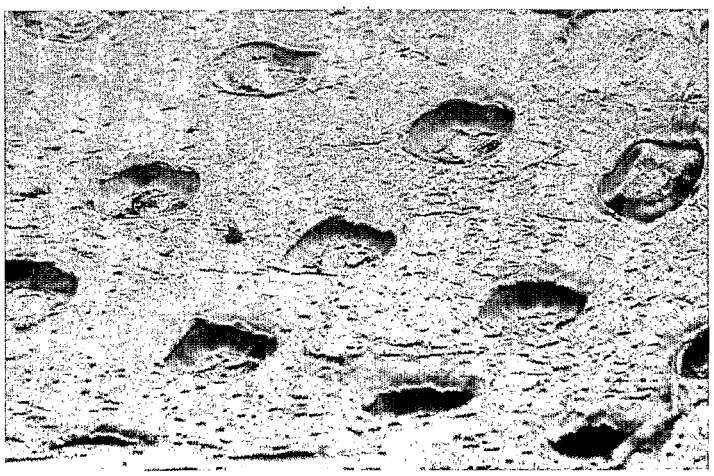

The microheaters of the present invention, one with a cone shape and one with the hollow posts, were applied to an in-vitro skin ablation experiment. FIG. 10 is a photomicrograph and FIGS. 11a and 11b is a scanning electron micrograph (SEM) of human cadaver skin (stratum corneum and epidermis) after the microheaters were applied to the skin, activated and removed. Two sites of local skin micro-ablation in the position of the conical tips and an array of donut-shaped openings in the shape of the tips of the hollow posts are shown in FIGS. 10 and 11a and 11b, respectively. The fabricated microheaters created localized micro-ablation in human skin.

Figure 12:
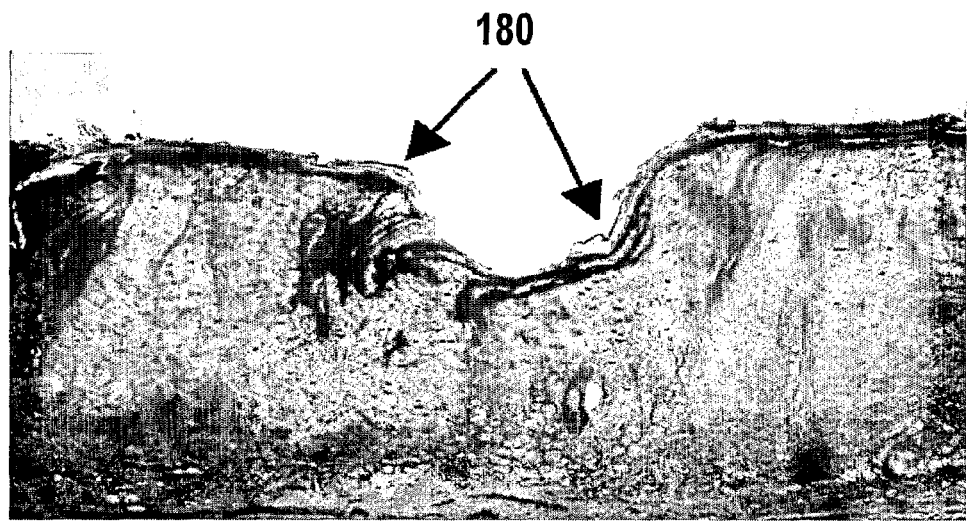
FIG. 12 is a photomicrograph of a histological section of rat skin after micropore formation using a cone-shaped microheater.

To simulate an in-vivo experiment, the conical microheater was applied and energized on the skin of a hairless rat immediately after death. The skin specimen was then removed and prepared for sectioning using a cryostat microtome. As shown in FIG. 12, the skin was indented due to pressing the cone-shaped microheater against the skin, and the stratum corneum was ablated along the surface of the indention.

Other methods can be used to measure effects of microheater treatment of skin. After exposure to thermal treatment by the present invention, skin can be examined histologically to determine the location and extent of ablation, as indicated by structural changes and darkened tissue color. The skin is fixed and sectioned with a cryostat microtome at a thickness of 10-14 μm. Skin slices are stained with hematoxalyn and eosin and cross-sectional images are collected by digital microscopy (Olympus). Using image analysis software (ImagePro Plus), the depth, width and total area of microablation is quantified for correlation with other experimental measurements and model predictions.

To determine the temperature profile in skin during microablation, a series of temperature-sensitive dyes (Licristal, Hallcrest) that can label the skin and undergo permanent color change if the temperature exceeds different threshold values can be used. Contour lines of peak temperatures in skin can be mapped and directly correlated with changes in histological features. An infrared camera for microscopic examination of the skin during microablation can be used to obtain kinetic information, but spatial information is limited primarily to the x-y axis parallel to the skin surface, with difficulty obtaining z-axis information into the depth of skin. Temperature profiles generated from these data are compared to histological data as well as predictions from theoretical models. The negative control can be skin contacted with non-activated heating elements and the positive control can be skin heated to various temperatures on a controlled hot plate.

Example 4

Microheater components are tested for use in ablation of stratum corneum and increasing barrier permeability and increased drug transport by assessing transport across cadaver skin by three different molecules. Calcein is a low molecular weight (623 Da) fluorescent molecule used to measure skin permeability by spectrofluorimetric assay and image transport pathways in skin by confocal microscopy. BSA (bovine serum albumin) (66 kDa) is a macromolecular protein that can be fluorescently labeled and used as a macromolecular companion to calcein to probe the effect of molecular size. Insulin is a polypeptide (6 kDa) that will be used for comparison with in vivo studies involving insulin delivery to diabetic rats. To perform skin permeability measurements, cadaver epidermis is placed in a Franz diffusion cell at 37° C. and an array of microheaters is then positioned on the stratum corneum side and thermally activated to cause microablation. The lower, receptor compartment is filled with 5 ml of well-stirred phosphate buffer saline, the receptor solution, and the upper, donor compartment is filled with a model drug solution. Every hour, or more frequently, 1 ml of receptor solution is sampled, and replaced with fresh saline, and fluorescence intensity is measured using calibrated spectrofluorometry and analyzed to determine rates of transdermal delivery. The micropores made by the activation of the microheaters are effective in reducing the barrier capability of the cadaver skin. Calcein, BSA and insulin, added individually to the donor compartment, are later measured in the receptor solution.

Example 5

Drug Delivery In Vivo.

The in vivo skin model is a Sprague-Dawley hairless rat, a commonly used model for human skin permeability due to the similarity of hairless rat and human skin. For initial studies, rats ARE anesthetized by intraperitoneal injection of urethane (1000 mg/kg) and treated with a thermal treatment device of the present invention. The skin is exposed either briefly to a blue tissue marking dye to visualize the size and location of pores, or exposed for over an hour to a calcein solution to image the transdermal transport process. After sacrificing the animal, skin specimens are excised and prepared for histological examination by cryostat sectioning. The skin from rats exposed to blue dye and skin from rats exposed to the calcein solution both show transport of the molecules into the micropores and with time, transport across the epidermis of the tissue sections.

For insulin delivery studies, rats are made diabetic by intravenous injection with 100 mg/kg streptozotocin, which produces diabetes the next day due to destruction of pancreatic islet cells. Under urethane anesthesia, skin is treated with a thermal treatment device of the present invention and the treated skin area is exposed to an Humulin-R insulin solution. Blood samples are collected by tail veil laceration over time to measure glucose concentration using a FreeStyle glucose monitor to determine pharmacodynamic response and to measure insulin concentration by radioimmunoassay to determine pharmacokinetic response, after which the animal is sacrificed. Control experiments include placement of insulin on skin which does not receive treatment using a thermal treatment device of the present invention, use of a thermal treatment device of the present invention with a saline solution instead of an insulin solution, no treatment, and intradermal injection of known amounts of insulin ranging from 10 mU to 10 U for calibration. Rats that received insulin through micropores made with a thermal treatment device of the present invention show insulin in the blood and response to glucose control.

Example 6

Fabrication of Excitation Coils with AC Power Source.

An excitation coil is needed to create magnetic fields that wirelessly activate the inductive microheaters. When the power supply component is placed above the skin and around the microheaters, the inner diameter of the coil must be large enough to contain the microheaters inside. In preliminary experiments, 1 cm inner diameter coil size was chosen that was suitable for initial heating experiments. The excitation coil was fabricated by hand-winding 100 turns of thin magnetic wire on a short epoxy tube. The coil was connected to a conventional AC power supply and when tested with AC current over the range of 1-2 A, it showed stable operation.

Other considerations for coil construction include the following. The excitation coil will be fabricated by conventionally winding conductor coils on optimally-shaped hollow polymer cores, optionally with incorporation of flux-guiding magnetic material. Coils are made with inner diameters of 1 cm, 3 cm, and 5 cm; cylinder height of 5 mm; 100 and 200 turns; and diameters of conductor wires 50 μm and 150 μm. The inner diameter of the coils may affect power supply characteristics. Multiple turn coils allow a tradeoff between current and wire length for a given magnetic flux generation, but have the potential for introduction of unwanted parasitics (e.g., conductor resistance or coil self-resonance) that could deleteriously affect efficiency or operation of the excitation coil. Variation of wire diameter allows determination of optimal conductor thickness, which could be a function of frequency due to the well-known skin effect limiting the efficacy of thick conductors in the MHz and higher frequency regimes.

Additional design constraints to be considered in the excitation coil system are size, frequency, and coil current. Off-the-shelf battery powered DC-AC switching inverters and RF amplifiers that are packaged and interconnected using conventional miniaturized printed circuit board technology can be utilized to produce the required time-varying coil currents. It should be noted that as in most magnetic systems, although currents are reasonably high (order 1 A), the voltages are low (<10 V), which maintains overall system safety.

Example 7

Computer Simulation for Thermal Analysis of Skin Heating

Figure 13:
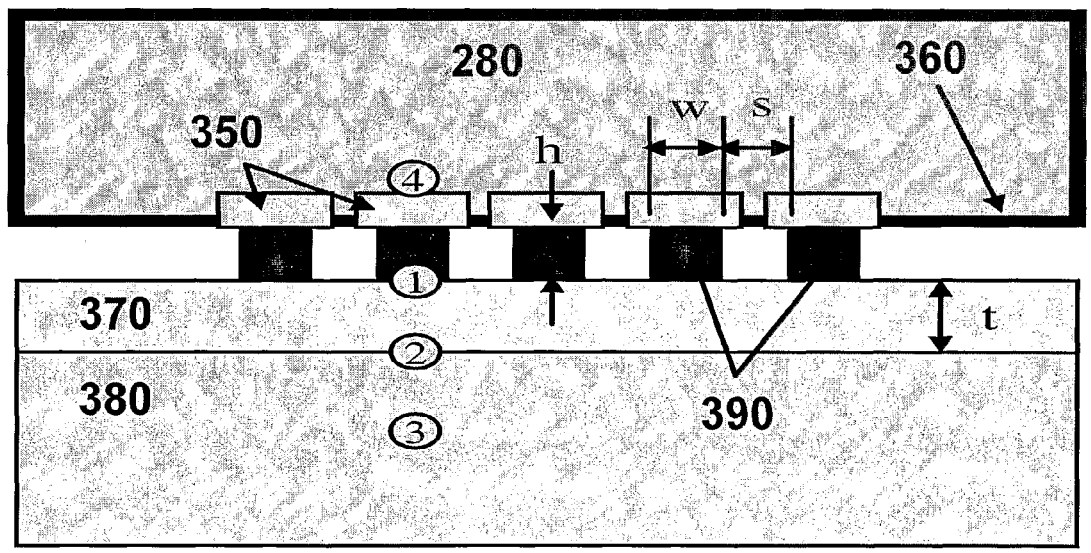
FIG. 13 is a schematic of heat transfer simulation (ANSYS) through skin by a heating element array.

Computer simulation using ANSYS software was used to model heat flows generated directly in heating elements and skin, as well as thermal diffusion from heating elements to skin and a neighboring drug reservoir. Safe and painless thermal microablation of skin requires delicate control of heat generation and transfer to ablate stratum corneum without damaging either deeper tissues or an active agent stored in the patch. To investigate the heat transfer properties through skin, a finite element thermal simulation was performed. FIG. 13 shows a schematic model of a metal heating element array attached to a drug-containing patch above and to skin below. Each heating element has a width w=100 μm, a height h=100 μm, and a space s=300 μm between neighboring elements. The thickness of epidermis is $t_{epi}$=80 μm and that of dermis $t_{derm}$=2 mm. Thermal properties of skin and other major materials used for the simulation are summarized in Table 2. For this preliminary temperature profile analysis, the energetics associated with phase transitions of water and other skin tissue components was not taken into account (a conservative assumption).

TABLE 2

Material Properties used for simulation of temperature profiles

| | Thermal conductivity [W/m · K] | Specific heat [J/Kg · K] | Density [Kg/m³] |
|---|---|---|---|
| Epidermis | 0.24 | 3590 | 1200 |
| Dermis | 0.45 | 3300 | 1200 |
| Metal (Ni) | 90.7 | 444 | 8900 |
| Thermal insulation | 0.03 | 1090 | 1420– |
| Air | 0.025 | 1040 | 0.616 |

Figure 14:
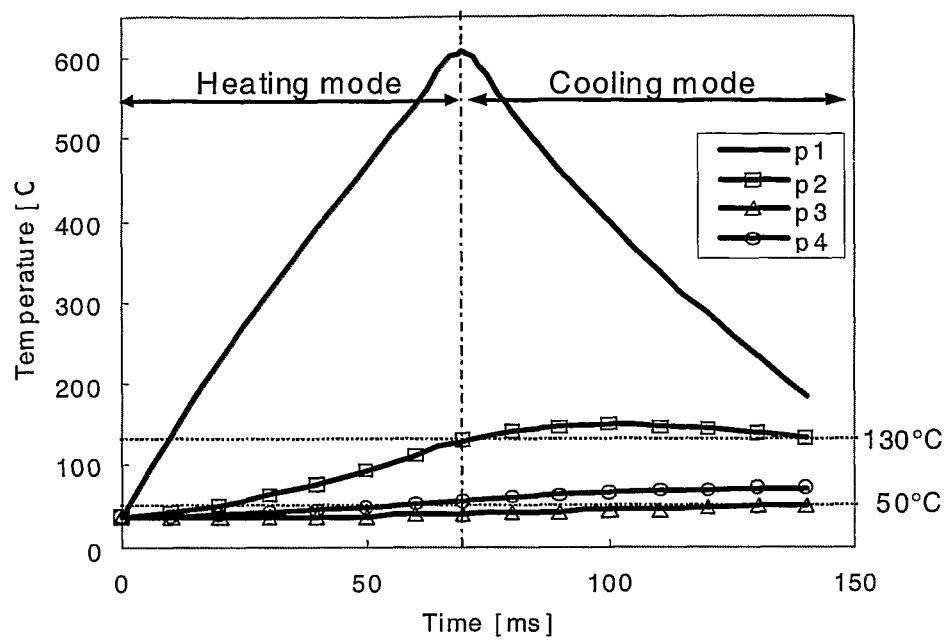
FIG. 14 shows transient thermal simulation of heat generation and cooling at the points indicated in FIG. 13.

Four points (labeled 1, 2, 3, and 4) were selected for temperature examination as shown in FIG. 13. Points 1, 2, and 3 are located at the interface between the microheater and the epidermis layer 370, between epidermis and dermis 380, and approximately 200 μm below epidermis, respectively. The insulation or thermal barriers 350 and the patch 360 containing an active agent 280 are shown Nerves are considered to exist at Point 3 and below. Point 4 is located approximately 200 μm above the heating elements within the patch drug matrix. The skin surface temperature needed for thermal ablation of skin is approximately 130° C., while the minimum temperature for nerve stimulation is approximately 40-50° C. The temperature range at which drugs might be damaged depends strongly on the type of drug. μm Given the constraints outlined above, we found that a microheater operating at 100 mS for 70 ms may be effective. As shown in FIG. 14, the temperature at point 2 reaches 130° C. in 70 ms while that of point 3 and 4 stay below 50° C. and 80° C., respectively. Consistent with literature findings, optimized conditions can microablate stratum corneum while protecting viable skin and drugs.

Thermal profiles in skin due to direct heating by magnetic field were simulated to be sure that the magnetic fields applied by the excitation coil only heat the microheaters, which in turn heat the skin, and do not have any direct effect on the skin which might cause uncontrolled heating in undesirable locations. A finite element analysis of eddy (inductive heating) current using ANSYS magnetic software was performed. The simulation model consists of a heating element, skin, and air. It was found that the eddy current vector is generated only on the heating element, not on the skin itself. Since there is no eddy current present in the skin, no inductive heating will be generated inside the skin. Since the frequency utilized for inductive heating is several orders of magnitude lower than the GHz/microwave frequencies associated with excitation of rotational modes of water, no heating is expected, nor was any observed, from this mechanism.

REFERENCES

R. Langer, "Drug delivery and targeting," Nature, 1998, 392, pp. 5-10

M. R. Prausnitz, S. Mitragotri and R. Langer, 'Current status and future potential of transdermal drug delivery," Nat Rev Drug Discov, 2004, 3, pp. 115-124

E. W. Smith and H. I. Maibach, Percutaneous Penetration Enhancers, CRC Press: Boca Raton, Fla., 1995

A. Naika, Y. N. Kalia, and R. H. Guy, "Transdermal drug delivery: overcoming the skin barrier function," PSTT 3: 318-326 (2000)

J. Bramson, K. Dayball, C. Evelegh, Y. H. Wan, D. Page, and A Smith, "Enabling topical immunization via microporation: a novel method for pain-free and needle-free delivery of adenovirus-based vaccines," Gene Ther, 2003, 10: 251-260

A. Zohar, "Transdermal drug delivery and analyte extraction," 2004, U.S. Pat. No. 6,711,435

S. Zinn and S. L. Semiatin, Elements of Induction Heating, Electric Power Research Institute, Palo Alto, Calif., 1988

J. Lammeraner, and M. Stafl, Eddy current, London: Iliffe Books Ltd., 1966, Chapter 2

J. A. Eppstein, M. R. Hatch, and D. Yang, "Microporation of human skin for drug delivery and monitoring applications," 2000, U.S. Pat. No. 6,142,939

E. W. Smith, et al., Percutaneous Enhancers, CRC Press, Boca Raton, Fla., (1995).

R. L. Bronaugh, et al., Percutaneou Absorption:Drus, Cosmetics, Mechanisms, Methodology, Marcel Dekker, NY, 992, (1999).

What is claimed is:

1. A method for increasing the permeability of a barrier, comprising the steps of:
    a) applying an effective amount of an ablation material to a selected site on a surface of a barrier;
    b) providing a thermal treatment device including a microheater component having at least one microheater, and positioning the thermal treatment device relative to the surface of the barrier;
    c) energizing the at least one microheater of the microheater component with a power supply component, wherein the power supply component is separate from the thermal treatment device and energizes the microheater component by creating a wireless magnetic field that interfaces between the power supply component and the microheater component; and
    d) heating the ablation material to a temperature from greater than 100° C. to about 200° C. to induce a phase change in the ablation material, thereby increasing the volume of the ablation material which is effective to ablate the surface of the barrier thereby increasing the permeability of the barrier.

2. The method of claim 1, wherein the barrier is selected from the group consisting of human skin, animal skin and mucous membrane.

3. The method of claim 1, wherein the ablation material is selected from the group consisting of liquids, gels, solutions, multiphase materials, and solids.

4. The method of claim 1 wherein the geometric configuration of the microheater is selected from the group consisting of a disk, a cone, a donut, a hollow post, and a loop, all of which range from less than 1 micron to hundreds of microns in length.

5. The method of claim 1, wherein the microheater is selected from the group consisting of single type metals, layers of metals, conductive oxides, conductive polymers or alloys, nickel, nickel-iron, ferromagnetic materials, copper, NiCu, PdCo, gadolinium-silicon-germanium alloy, aluminum, ceramic materials, electrodeposited or vapor-deposited gold, platinum, or palladium, outer layer coatings of nickel or nickel iron, magnetic stainless steel-type alloy, 4OO-series alloy, indium tin oxide, lanthanum strontium cobalt oxide, and aluminum doped zinc oxide.

6. A method for increasing the permeability of a barrier, comprising the steps of:
    a) providing a microheater component including at least one microheater having an ablation material disposed therein;
    b) energizing the microheater component with a power supply component, wherein the power supply component is separate from the microheater component and energizes the microheater component by creating a wireless magnetic field that interfaces between the power supply component and the microheater component; and c) heating the ablation material to a temperature from greater than 100° C. to about 200° C. to induce a phase change in the ablation material, thereby increasing the volume of the ablation material which, in turn, ablates the surface of the barrier thereby increasing the permeability of the barrier.

7. A thermal treatment device, comprising:
a) a microheater component including at least one microheater having a thermal member including a base end and a tip end;
b) an ablation material in contact with the microheater, wherein a volume of the ablation material increases upon heating the ablation material to a temperature from greater than 100° C. to about 200° C. to induce a phase change within the ablation material; and
c) a power supply component which is configured to activate the at least one microheater of the microheater component, wherein the power supply component is separate from the microheater component and activates the microheater component by creating a wireless magnetic field that interfaces between the power supply component and the microheater component.

8. The device of claim 7, wherein the ablation material is selected from the group consisting of liquids, gels, solutions, multiphase materials, and solids.

9. The device of claim 7, wherein the ablation material contacts an open space area of the microheater.

10. The device of claim 7, wherein the ablation material contacts a tip end of the microheater.

11. The device of claim 7, wherein the geometric configuration of the microheater is selected from the group consisting of a disk, a cone, a donut, a hollow post, and a loop, all of which range from less than 1 micron to hundreds of microns in length.

12. The device of claim 7, wherein the microheater is selected from the group consisting of single type metals, layers of metals, conductive oxides, conductive polymers or alloys, nickel, nickel-iron, ferromagnetic materials, copper, NiCu, PdCo, gadolinium-silicon-germanium alloy, aluminum, ceramic materials, electrodeposited or vapor-deposited gold, platinum, or palladium, outer layer coatings of nickel or nickel iron, magnetic stainless steel-type alloy, 400-series alloy, indium tin oxide, lanthanum strontium cobalt oxide, and aluminum doped zinc oxide.

* * * * *